(12) United States Patent
Ribble et al.

(10) Patent No.: US 11,007,097 B2
(45) Date of Patent: May 18, 2021

(54) DYNAMIC APNEA THERAPY SURFACE

(71) Applicant: Hill-Rom Services, Inc., Batesville, IN (US)

(72) Inventors: David L. Ribble, Indianapolis, IN (US); Michael S. Hood, Batesville, IN (US); Charles A. Howell, Batesville, IN (US); Eric D. Agdeppa, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 261 days.

(21) Appl. No.: 16/372,721

(22) Filed: Apr. 2, 2019

(65) Prior Publication Data

US 2019/0224060 A1 Jul. 25, 2019

Related U.S. Application Data

(62) Division of application No. 14/848,513, filed on Sep. 9, 2015, now Pat. No. 10,292,881.

(Continued)

(51) Int. Cl.
*A61G 7/015* (2006.01)
*A61G 7/018* (2006.01)
(Continued)

(52) U.S. Cl.
CPC ............ *A61G 7/015* (2013.01); *A61B 5/4809* (2013.01); *A61B 5/4812* (2013.01); *A61B 5/4818* (2013.01); *A61B 5/6892* (2013.01); *A61G 7/001* (2013.01); *A61G 7/018* (2013.01); *A61G 13/08* (2013.01); *A61G 7/008* (2013.01); *A61G 7/05776* (2013.01); *A61G 13/04* (2013.01); *A61M 21/02* (2013.01)

(58) Field of Classification Search
CPC ........ A61G 7/001; A61G 7/002; A61G 7/008; A61G 7/015; A61G 7/018; A61G 7/05769; A61G 13/02; A61G 13/04; A61G 13/08; A47C 27/10; A47C 27/081; A47C 27/082; A47C 27/083; A61B 5/4809; A61B 5/4812; A61B 5/4818; A61B 5/6892
USPC .... 5/616, 617, 618, 613, 607, 600, 710, 713
See application file for complete search history.

(56) References Cited

U.S. PATENT DOCUMENTS

| | | |
|---|---|---|
| 3,775,785 A | 12/1973 | Mittendorf |
| 4,754,510 A | 7/1988 | King |

(Continued)

FOREIGN PATENT DOCUMENTS

| | | |
|---|---|---|
| DE | 4137631 | 5/1992 |
| EP | 262771 | 4/1991 |

(Continued)

OTHER PUBLICATIONS

Adesanya, Adebola O., et al., *Perioperative Management of Obstructive Sleep Apnea*, Chest/138/6, Dec. 2010 (10 pages).

(Continued)

*Primary Examiner* — Robert G Santos
(74) *Attorney, Agent, or Firm* — Barnes & Thornburg LLP

(57) ABSTRACT

Dynamic support surface technologies configure a person support surface in various ways, including configurations in which the person support surface at least temporarily assumes an apnea therapy position, such as a progressive lateral tilt or a ramp-like position.

20 Claims, 12 Drawing Sheets

Related U.S. Application Data

(60) Provisional application No. 62/073,565, filed on Oct. 31, 2014.

(51) Int. Cl.
*A61B 5/00* (2006.01)
*A61G 13/08* (2006.01)
*A61G 7/008* (2006.01)
*A61G 7/057* (2006.01)
*A61G 13/04* (2006.01)
*A61G 7/00* (2006.01)
A61M 21/02 (2006.01)

(56) References Cited

U.S. PATENT DOCUMENTS

| | | | |
|---|---|---|---|
| 4,807,313 A | 2/1989 | Ryder et al. |
| 4,941,221 A | 7/1990 | Kanzler |
| 5,092,007 A | 3/1992 | Hasty |
| 5,097,551 A | 3/1992 | Smith |
| 5,611,096 A | 3/1997 | Bartlett et al. |
| 5,640,729 A | 6/1997 | Mariño |
| 5,745,937 A | 5/1998 | Weismiller et al. |
| 5,754,998 A | 5/1998 | Selton |
| 5,910,080 A | 6/1999 | Selton |
| 5,966,762 A | 10/1999 | Wu |
| 6,047,419 A | 4/2000 | Ferguson |
| 6,081,950 A | 7/2000 | Selton |
| 6,154,900 A | 12/2000 | Shaw |
| 6,163,903 A | 12/2000 | Weismiller et al. |
| D446,676 S | 8/2001 | Mayes |
| 6,370,716 B1 | 4/2002 | Wilkinson |
| 6,485,441 B2 | 11/2002 | Woodward |
| 6,536,056 B1 | 3/2003 | Vrzalik et al. |
| 6,578,219 B1 | 6/2003 | Gabel et al. |
| 6,671,907 B1 | 1/2004 | Zuberi |
| 6,681,424 B1 | 1/2004 | Bourgraf et al. |
| 6,751,817 B1 | 6/2004 | Leach |
| 6,904,631 B2 | 6/2005 | Vrzalik et al. |
| 7,007,327 B2 | 3/2006 | Ogawa et al. |
| 7,017,213 B2 | 3/2006 | Chisari |
| 7,089,615 B1 | 8/2006 | Parimuha |
| D527,937 S | 9/2006 | Aiken et al. |
| 7,346,945 B2 | 3/2008 | Phillips et al. |
| 7,418,751 B1 | 9/2008 | Bartlett et al. |
| 7,464,422 B2 | 12/2008 | Townsend |
| 7,513,003 B2 | 4/2009 | Mossbeck |
| 7,654,974 B2 | 2/2010 | Bass |
| 7,690,059 B2 | 4/2010 | Lemire et al. |
| 7,805,784 B2 | 10/2010 | Lemire et al. |
| 7,861,334 B2 | 1/2011 | Lemire et al. |
| 7,886,379 B2 | 2/2011 | Benzo et al. |
| 7,962,981 B2 | 6/2011 | Lemire et al. |
| 7,975,335 B2 | 7/2011 | O'Keefe et al. |
| 8,006,332 B2 | 8/2011 | Lemire et al. |
| 8,220,091 B2 | 7/2012 | Schultz |
| 8,261,380 B2 | 9/2012 | Ferraresi et al. |
| 8,356,602 B2 | 1/2013 | Crocetti |
| 8,393,026 B2 | 3/2013 | Dionne et al. |
| 8,413,271 B2 | 4/2013 | Blanchard et al. |
| 8,544,126 B2 | 10/2013 | Elliott et al. |
| 8,661,586 B2 | 3/2014 | Melcher et al. |
| 8,689,376 B2 | 4/2014 | Becker et al. |
| 8,695,134 B2 | 4/2014 | Schultz |
| 8,701,229 B2 | 4/2014 | Lemire et al. |
| 8,720,447 B2 | 5/2014 | North |
| 8,756,736 B1 | 6/2014 | Minson |
| 8,789,222 B2 | 7/2014 | Blanchard et al. |
| 8,832,887 B2 | 9/2014 | Mossbeck |
| 8,844,076 B2 | 9/2014 | Becker et al. |
| 8,870,764 B2 | 10/2014 | Rubin |
| 8,978,184 B1 | 3/2015 | Garrett |
| 9,038,217 B2 | 5/2015 | Elliot et al. |
| 9,126,571 B2 | 9/2015 | Lemire et al. |
| 10,292,881 B2 | 5/2019 | Ribble et al. |
| 10,660,807 B2 * | 5/2020 | Ribble ............... A61G 7/0509 |
| 2004/0031103 A1 | 2/2004 | Wyatt et al. |
| 2004/0103475 A1 | 6/2004 | Ogawa et al. |
| 2006/0179580 A1 | 8/2006 | Robertson et al. |
| 2007/0163043 A1 | 7/2007 | Lemire et al. |
| 2007/0163051 A1 | 7/2007 | Straub |
| 2008/0109965 A1 | 5/2008 | Mossbeck |
| 2008/0148487 A1 | 6/2008 | Lord et al. |
| 2009/0144909 A1 | 6/2009 | Skinner et al. |
| 2009/0250070 A1 | 10/2009 | Pfeifer |
| 2011/0035057 A1 | 2/2011 | Receveur et al. |
| 2011/0231996 A1 | 9/2011 | Lemire et al. |
| 2011/0263950 A1 | 10/2011 | Larson et al. |
| 2011/0301440 A1 | 12/2011 | Riley et al. |
| 2012/0073054 A1 | 3/2012 | O'Keefe et al. |
| 2012/0138067 A1 | 6/2012 | Rawls-Meehan |
| 2012/0222214 A1 | 9/2012 | Lachenbruch et al. |
| 2013/0198965 A1 | 8/2013 | Melcher et al. |
| 2013/0245395 A1 | 9/2013 | Bidarian Moniri |
| 2013/0267791 A1 | 10/2013 | Halperin et al. |
| 2014/0059768 A1 | 3/2014 | Lemire et al. |
| 2014/0088373 A1 | 3/2014 | Phillips et al. |
| 2014/0173829 A1 | 6/2014 | Melcher et al. |
| 2014/0180036 A1 | 6/2014 | Bukkapatnam et al. |
| 2014/0245539 A1 | 9/2014 | Ooba |
| 2014/0259417 A1 | 9/2014 | Nunn et al. |
| 2014/0259418 A1 | 9/2014 | Nunn et al. |
| 2014/0259419 A1 | 9/2014 | Stusynski et al. |
| 2014/0259433 A1 | 9/2014 | Nunn et al. |
| 2014/0259434 A1 | 9/2014 | Nunn et al. |
| 2014/0266733 A1 | 9/2014 | Hayes et al. |
| 2014/0277611 A1 | 9/2014 | Nunn et al. |
| 2014/0277822 A1 | 9/2014 | Nunn et al. |
| 2014/0283302 A1 | 9/2014 | Horstmann |
| 2014/0345060 A1 | 11/2014 | Ribble et al. |
| 2014/0366274 A1 | 12/2014 | Melcher et al. |
| 2015/0000035 A1 | 1/2015 | Becker et al. |
| 2015/0136146 A1 | 5/2015 | Hood et al. |
| 2015/0335507 A1 | 11/2015 | Emmons et al. |
| 2016/0120716 A1 | 5/2016 | Ribble et al. |
| 2019/0224060 A1 * | 7/2019 | Ribble ............... A61G 7/001 |
| 2020/0360207 A1 * | 11/2020 | Hood ............... A61B 5/747 |

FOREIGN PATENT DOCUMENTS

| | | |
|---|---|---|
| EP | 2175822 B1 | 1/2012 |
| EP | 2140847 B1 | 7/2012 |
| EP | 2494946 | 9/2012 |
| JP | 2011-143237 | 7/2011 |
| JP | WO2013031504 A1 | 7/2013 |
| KR | 20110083167 | 7/2011 |
| WO | WO 2010/048310 | 4/2010 |
| WO | WO 2013/166003 | 4/2013 |
| WO | WO 2013/116676 | 8/2013 |
| WO | WO 2013/177338 | 11/2013 |
| WO | WO 2014/069713 | 5/2014 |
| WO | WO 2014/151707 | 9/2014 |
| WO | WO 2014/152891 | 9/2014 |
| WO | WO 2014/149392 | 11/2014 |

OTHER PUBLICATIONS

Ankichetty, Saravanan and Frances Chung, *Considerations for Patients with Obstructive Sleep Apnea Undergoing Ambulatory Surgery*, Current Opinion in Anesthesiology 2011, 24:605-611 (7 pages).

Arnold, Donald H., et al., *Estimation of Airway Obstruction Using Oximeter Plethysmograph Waveform Data*, Respiratory Research 2005, 6:65 (8 pages).

American Society of Anesthesiologists, Inc., *Practice Guidelines for the Perioperative Management of Patients with Obstructive Sleep Apnea*, Anesthesiology 2006, V. 104, 1081-93, No. 5, May 2006, (13 pages).

Benumof, Jonathan L., *Obstructive Sleep Apnea in the Adult Obese Patient: Implications for Airway Management*, Journal of Clinical Anesthesia 13:144-156, 2001 (13 pages).

(56) References Cited

OTHER PUBLICATIONS

Berend, Keith R., et al., *Prevalence and Management of Obstructive Sleep Apnea in Patients Undergoing Total Joint Arthroplasty*, The Journal of Arthroplasty vol. 25 No. 6 Suppl. 1 2010 (4 pages).
Berger, G., et al., *Progression of Snoring and Obstructive Sleep Apnoea: The Role of Increasing Weight and Time*, European Respiratory Journal, vol. 33, No. 2, 2009 (8 pages).
Bianchi, Matt T., *Screening for Obstructive Sleep Apnea: Bayes Weighs in*, The Open Sleep Hournal, 2009, 2, 56-59 (4 pages).
Bignold, James J., et al., *Accurate Position Monitoring and Improved Supine-Dependent Obstructive Sleep Apnea with a New Position Recording and Supine Avoidance Device*, Journal of Clinical Sleep Medicine, vol. 7, No. 4, 2001 (8 pages).
Bloom, Harrison G., et al., *Evidence-Based Recommendations for the Assessment and Management of Sleep Disorders in Older Persons*, J Am Geriatr Soc 57:761-789, 2009 (30 pages).
Bolden, Norman, et al., *Avoiding Adverse Outcomes in Patients with Obstructive Sleep Apnea (OSA): Development and Implementation of a Perioperative OSA Protocol*, Journal of Clinical Anesthesia (2009) 21, 286-293 (8 pages).
Bourne, Richard S., et al., *Clinical Review: Sleep Measurement in Critical Care Patients: Research and Clinical Implications*, Critical Care 2007, 11:226 (17 pages).
Brown, Carlos VR and George C. Velmahos, *The Consequences of Obesity on Trauma, Emergency Surgery, and Surgical Critical Care*, World Journal of Emergency Surgery 2006, 1:27 (5 pages).
Bush, Haydn, *Screening for Sleep Apnea*, American Hospital Association Health Forum, Hospital & Health Networks, hhn@omeda.com, 2013 (2 pages).
Camilo, Millene R., et al., *Supine Sleep and Positional Sleep Apnea After Acute Ischemic Stroke and Intracerebral Hemorrhage*, Clinics 2012; 67(12); 1357-1360 (4 pages).
Carr, Gordon E., et al., *Acute Cardiopulmonary Failure From Sleep-Disordered Breathing*, Chest 2012; 141(3); 798-808 (11 pages).
Casey, Kenneth R. and Michael J. Lefor, *Management of the Hospitalized Patient with Sleep Disordered Breathing*, Current Opinion in Pulmonary Medicine 2002, 8:511-515 (5 pages).
Chia, P., et al., *The Association of Pre-Operative STOP-BANG Scores with Postoperative Critical Care Admission*, Anaesthesia 2013, 68, 950-952 (3 pages).
Choi, Jae-Kap, et al., *Effect of Jaw and Head Position on Airway Resistance in Obstructive Sleep Apnea*, Sleep and Breathing, vol. 4, No. 4, 163-168, 2000 (8 pages).
Choi, Ji Ho, et al., *Efficacy Study of a Vest-Type Device for Positional Therapy in Position Dependent Snorers*, Sleep and Biological Rhythms 2009; 7; 181-187 (7 pages).
Chung, Sharon A., et al., *A Systemic Review of Obstructive Sleep Apnea and Its Implications for Anesthesiologists*, Ambulatory Anesthesiology, vol. 107, No. 5, Nov. 2008, 1543-1563 (21 pages).
Chung, F., et al., *High STOP-Band Score Indicates a High Probability of Obstructive Sleep Apnoea*, British Journal of Anaesthesia 108 (5): 768-75 (2012), (8 pages).
Chung, Frances and Babak Mokhlesi, *Postoperative Complications Associates with Obstructive Sleep Apnea: Time to Wake Up!*, Anesthesia & Analgesia, Feb. 2014, vol. 118, No. 2, 251-253 (3 pages).
Chung, Frances et al., *Preoperative Identification of Sleep Apnea Risk in Elective Surgical Patient6s, Using the Berlin Questionnaire*, Journal of Clinical Anesthesia (2007) 19, 130-134 (5 pages).
Chung, Frances and Hisham Elsaid, *Screening for Obstructive Sleep Apnea Before Surgery: Why is it Important?*, Current Opinion in Anaesthesiology 2009, 22:405-411 (7 pages).
Chung, Frances, et al., *Validation of the Berlin Questionnaire and American Society of Anesthesiologists Checklist as Screening Tools for Obstructive Sleep Apnea in Surgical Patients*, Anesthesiology, vol. 108, No. 5, May 2008, 822-830 (9 pages).
Curry, J. Paul and Lawrence A. Lynn, *Threshold Monitoring, Alarm Fatigue, and the Patterns of Unexpected Hospital Death*, The Official Journal of the Anesthesia Patient Safety Foundation, Fall 2011 (8 pages).

D'Apuzzo, Michele R. and James A. Browne, *Obstructive Sleep Apnea as a Risk Factor for Postoperative Complications After Revision Joint Arthroplasty*, The Journal of Arthroplasty, vol. 27, No. 8, Suppl. 1 (2012), 95-98 (4 pages).
Der Herder, Cindy, et al., *Risks of General Anaesthesia in People with Obstructive Sleep Apnoea*, British Medical Journal, vol. 329, Oct. 23, 2004, 955-959 (5 pages).
Dolezal, Donna, et al., *Implementing Preoperative Screening of Undiagnosed Obstructive Sleep Apnea*, Journal of PeriAnesthesia Nursing, vol. 26, No. 5 Oct. 2011, 338-342 (5 pages).
Ead, Heather, *Meeting the Challenge of Obstructive Sleep Apnea: Developing a Protocol that Guides Perianesthesia Patient Care*, Journal of PeriAnesthesia Nursing, vol. 24, No. 2 Apr. 2009, 103-113 (11 pages).
Farney, Robert J., et al., *The STOP-Bang Equivalent Model and Prediction of Severity of Obstructive Sleep Apnea: Relation to Polysomnographic Measurements of the Apnea/Hypopnea Index*, Journal of Clinical Sleep Medicine, vol. 7, No. 5, 2011, 459-467 (9 pages).
Finkel, Kevin J., et al., *Prevalence of Undiagnosed Obstructive Sleep Apnea Among Adult Surgical Patients in an Academic Medical Center*, Sleep Medicine 10 (2009) 753-758 (6 pages).
Finucane, Thomas E., *Evidence-Based Recommendations for the Assessment and Management of Sleep Disorders in Older Persons*, JAGS, Nov. 2009, vol. 57, No. 11, 2173-2174 (3 pages).
Fletcher, Eugene C., *"Near Miss" Death in Obstructive Sleep Apnea: A Critical Care Syndrome*, Critical Care Medicine, vol. 19, No. 9, Sep. 1991, 1158-1164 (7 pages).
Galhotra, Sanjay, *Mature Rapid Response System and Potentially Avoidable Cardiopulmonary Arrests in Hospital*, Qual. Saf. Health Care 2007, 16:260-265 (6 pages).
Gammon, Brian T. and Karen F. Ricker, *An Evidence-Based Checklist for the Postoperative Management of Obstructive Sleep Apnea*, Journal of PeriAnesthesia Nursing, vol. 27, No. 5 Oct. 2012, 316-322 (7 pages).
Gay, Peter C., *Sleep and Sleep-Disordered Breathing in the Hospitalized Patient*, Respiratory Care, Sep. 2010, vol. 55, No. 9, 1240-1254 (15 pages).
Gay, Peter C., *The Value of Assessing Risk of Obstructive Sleep Apnea in Surgical Patients: It Only Takes One*, Journal of Clinical Sleep Medicine, vol. 6, No. 5, 2010, 473-474 (2 pages).
Global Industry Analysts, Inc., *GIA Market Report: Sleep Apnea Diagnostic and Therapeutic Devices, A Global Strategic Business Report*, MCP-3307, Oct. 2010, www.StrategyR.com, (321 pages).
Gibson, G. J., *Obstructive Sleep Apnoea Syndrome: Underestimated and Undertreated*, British Medical Bulletin 2004; 72: 49-64 (16 pages).
Gupta, Rakesh M., et al., *Postoperative Complications in Patients With Obstructive Sleep Apnea Syndrome Undergoing Hip or Knee Replacement: A Case-Control Study*, May Clin Proc. 2001; 76:897-905 (9 pages).
Guralnick, Amy S., et al., *CPAP Adherence in Patients with Newly Diagnosed Obstructive Sleep Apnea Prior to Elective Surgery*, Journal of Clinical Sleep Medicine, vol. 8, No. 5, 2012, 501-506 (6 pages).
Heinzer, Raphael C., et al., *Positional Therapy for Obstructive Sleep Apnea: An Objective Measurement of Patients' Usage and Efficacy at Home*, Sleep Medicine 13 (2012) 425-428 (4 pages).
Hoque, Enamul, et al., *Monitoring Body Positions and Movements During Sleep Using WISPs*, Wireless Health '10, Oct. 5-7, 2010 (10 pages).
Isono, Shiroh, et al., *Lateral Position Decreases Collapsibility of the Passive Pharynx in Patients with Obstructive Sleep Apnea*, Anesthesiology, vol. 97, No. 4, Oct. 2002, 780-785 (6 pages).
Itasaka, Yoshiaki and Kazuo Ishikawa, *The Influence of Sleep Position and Obesity on Sleep Apnea*, Psychiatry and Clinical Neurosciences (2000), 54, 340-341 (3 pages).
Jensen, Candice, et al., *Postoperative CPAP and BiPAP Use Can be Safely Omitted after Laparoscopic Roux-en-Y Gastric Bypass*, Surgery for Obesity and Related Diseases 4 (2008) 512-514 (3 pages).
Joho, Shuji, et al., *Impact of Sleeping Position on Central Sleep Apnea/Cheyne-Stokes Respiration in Patients with Heart Failure*, Sleep Medicine 11 (2010) 143-148 (6 pages).

(56) References Cited

OTHER PUBLICATIONS

Jokie, Ruzica, et al., *Positional Treatment vs. Continuous Positive Airway Pressure in Patients with Positional Obstructive Sleep Apnea Syndrome*, Chest/115/3/Mar. 1999, 771-781 (11 pages).
Joosten, S.A., et al., *Obstructive Sleep Apnea Phenotypic Trait Changes from Supine to Lateral Position*, Am J Respir Crit Care Med 189; 2014; A3909 (1 page).
Joshi, Girish P., et al., *Society for Ambulatory Anesthesia Consensus Statement on Preoperative Selection of Adult Patients with Obstructive Sleep Apnea Scheduled for Ambulatory Surgery*, Anesthesia & Analgesia, Nov. 2012, vol. 115, No. 5, 1060-1068 (9 pages).
Keenan, Sean P., et al., *Clinical Practice Guidelines for the Use of Noninvasive Positive-Pressure Ventilation and Noninvasive Continuous Positive Airway Pressure in the Acute Care Setting*, Canadian Medical Association Journal, Feb. 22, 2011, 183(3) (21 pages).
Khayat, Rami, et al., *In-Hospital Resting for Sleep-Disordered Breathing in Hospitalized Patients with Decompensated Heart Failure*: Report of Prevalence and Patient Characteristics, Journal of Cardiac Failure, vol. 15, No. 9 (2009) (739-746).
Kim, Eun Joong, *The Prevalence and Characteristics of Positional Sleep Apnea in Korea*, Korean J Otorhinolaryngol-Head Neck Surg. 2009:52:407-12 (6 pages).
Kulkarni, Gaurav V., et al., *Obstructive Sleep Apnea in General Surgery Patients: Is it More Common than we Think?*, The American Journal of Surgery (2014) 207, 436-440 (5 pages).
Lakdawala, Linda, *Creating a Safer Perioperative Environment With an Obstructive Sleep Apnea Screening Tool*, Journal of PeriAnesthesia Nursing, vol. 26, No. 1 Feb. 2001, 15-24 (10 pages).
Lee, Chul Hee, et al., *Changes in Site of Obstruction in Obstructive Sleep Apnea Patients According to Sleep Position: A DISE Study*, Laryngoscope 00: Month 2014 (7 pages).
Lee, Jung Bok, et al., *Determining Optimal Sleep Position in Patients with Positional Sleep-Disordered Breathing Using Response Surface Analysis*, J. Sleep Res. (2009) 18, 26-35 (10 pages).
Lockhart, Ellen M., et al. *Obstructive Sleep Apnea Screening and Postoperative Mortality in a Large Surgical Cohort*, Sleep Medicine 14 (2013) 407-415 (9 pages).
Lynn, Lawrence A. and J. Paul Curry, *Patterns of Unexpected In-Hospital Deaths: A Root Cause Analysis*, Patient Safety in Surgery 2011, 5:3 (25 pages).
Mador, M. Jeffrey, et al., *Are the Adverse Effects of Body Position in Patients with Obstructive Sleep Apnea Dependent on Sleep Stage?*, Sleep Breath (2010) 14:13-17 (7 pages).
Mador, M. Jeffrey, et al., *Prevalence of Positional Sleep Apnea in Patients Undergoing Polysomnography*, Chest 2005; 128:2130-2137 (8 pages).
Marcus, Howard, *Obesity and Postoperative Surgical Risk*, The Doctors Company, Third Quarter 2010, 1-8 (8 pages).
Martin-Du Pan, Rémy, et al., *The Role of Body Position and Gravity in the Symptoms and Treatment of Various Medical Diseases*, Swiss Med. Wkly. 2004: 134:543-551 (10 pages).
Memtsoudis, Stavros G., et al., *A Rude Awakening—The Perioperative Sleep Apnea Epidemic*, N Engl. J. Med. 368:25, 2352-2353 (Jun. 20, 2013) (2 pages).
Menon, Akshay and Manoj Kumar, *Influence of Body Position on Severity of Obstructive Sleep Apnea: A Systematic Review*, Otolaryngology, vol. 2013, Article ID 670381 (2013) (8 pages).
Mininni, Nicolette C., et al., *Pulse Oximetry: An Essential Tool for the Busy Med-Surg Nurse*, American Nurse Today, Nov./Dec. 2009, 31-33 (3 pages).
Mokhlesi, Babak, *Empiric Postoperative Autotitrating Positive Airway Pressure Therapy / Generating Evidence in the Perioperative Care of Patients at Risk for Obstructive Sleep Apnea*, Chest 144/1 (Jul. 2013) 5-7 (3 pages).
Mull, Yvonne and Marshall Bedder, *Obstructive Sleep Apnea Syndrome in Ambulatory Surgical Patients*, AORN Journal, vol. 76, No. 3, 458-462 (Sep. 2002) (5 pages).

Nader, Nizar Z., et al., *Newly Identified Obstructive Sleep Apnea in Hospitalized Patients: Analysis of an Evaluation and Treatment Strategy*, Journal of Sleep Medicine, vol. 2, No. 4, 2006, 431-437 (7 Pages).
Pevernagie, Dirk A., et al., *Effects of Body Position on the Upper Airway of Patients with Obstructive Sleep Apnea*, Am J Respir Crit Care Med, vol. 152, 179-185, 1995 (7 pages).
Qureshi, Asher and Robert D. Ballard, *Obstructive Sleep Apnea*, J Allergy Clin Immunol, vol. 112, No. 4, 643-651 (2003) (9 pages).
Richard, Wietske, et al., *The Role of Sleep Position in Obstructive Sleep Apnea Syndrome*, Eur Arch Otorhinolaryngol (2006) 263:946-950 (5 pages).
Rocke, Daniel, et al., *Effectiveness of a Postoperative Disposition Protocol for Sleep Apnea Surgery*, American Journal of Otolaryngology—Head and Neck Medicine and Surgery 34 (2013) 273-277 (5 pages).
Gabbott, D.A., *The Effect of Single-Handed Cricoid Pressure on Neck Movement After Applying Manual In-Line Stabilisation*, Anaesthesia, 1997, 52, 586-602 (17 pages).
Ross, Jacqueline, *Obstructive Sleep Apnea: Knowledge to Improve Patient Outcomes*, Journal of PeriAnesthesia Nursing, vol. 23, No. 4 Aug. 2008, 273-275 (3 pages).
Setaro, Jill, *Obstructive Sleep Apnea: A Standard of Care That Works*, Journal of PeriAnesthesia Nursin. vol. 27, No. 5 Oct. 2012, 323-328 (6 pages).
Sheldon, Alison, et al., *Nursing Assessment of Obstructive Sleep Apnea in Hospitalised Adults: A Review of Risk Factors and Screening Tools*, Contemporary Nurse, vol. 34, Issue 1, Dec. 2009/Jan. 2010, 19-33 (16 pages).
Skinner, Margot A., et al., *Efficacy of the 'Tennis Ball Technique' Versus nCPAP in the Management of Position-Dependent Obstructive Sleep Apnoea Syndrome*, Respirology (2008) 13, 708-715 (8 pages).
Stearns, Joshua D. and Tracey L. Stierer, *Peri-Operative Identification of Patients at Risk for Obstructive Sleep Apnea*, Seminars in Anesthesia, Perioperative Medicine and Pain (2007) 26, 73-82 (10 pages).
Van Kesteren, Ellen R., et al., *Quantitative Effects of Trunk and Head Position on the Apnea Hypopnea Index in Obstructive Sleep Apnea*, Sleep, vol. 34, No. 8 (2011), 1075-1081 (7 pages).
Veasey, Sigrid C., et al., *Medical Therapy for Obstructive Sleep Apnea: A Review by the Medical Therapy for Obstructive Sleep Apnea Task Force of the Standards of Practice Committee of the American Academy of Sleep Medicine*, Sleep, vol. 29, No. 8 (2006), 1036-1044 (9 pages).
Wolfson, Alexander, et al., *Postoperative Analgesia for Patients with Obstructive Sleep Apnea Syndrome*, Seminars in Anesthesia, Perioperative Medicine and Pain (2007), 26, 103-109 (7 pages).
Yantis, Mary Ann, *Decreasing Surgical Risks for Patients with Obstructive Sleep Apnea*, AORN Journal, vol. 68, No. 1 (Jul. 1998), 50-55 (6 pages).
Ravesloot, M.J.L., and N. de Vries, *Reliable Calculation of the Efficacy of Non-Surgical Treatment of Obstructive Sleep Apnea Revisted*, Sleep, vol. 34, No. 1 (2011), 105-110 (6 pages).
Moon, Il Joon, et al., *Sleep Magnetic Resonance Imagine as a New Diagnostic Method in Obstructive Sleep Apnea Syndrome*, Laryngoscope 120: Dec. 2010, 2546-2554 (9 pages).
Nepomnayshy, Dmitry, et al., *Sleep Apnea: Is Routine Preoperative Screening Necessary?*, OBES Surg (2013) 23:287-192 (5 pages).
Press Release: *World's Leading Health Media Promotes Disinformation on Best Sleeping Positions* (Sep. 22, 2010), Sleeping Positions Research Summary (24 Studies), http://www.normalbreathing.com/1-6-best-sleep-positions.php (14 pages).
Oksenberg, Arie, et al., *Association of Body Position with Severity of Apneic Events in Patients with Severe Nonpositional Obstructive Sleep Apnea*, Chest 2000; 118; 1018-1024 (9 pages).
Oksenberg, Arie, *The Avoidance of the Supine Posture during Sleep for Patients with Supine-related Sleep Apnea*, BSM Protocols for Adherence and Treatment of Intrinsic Sleep Disorders, Chapter 23, 223-236 (14 pages).

(56) References Cited

OTHER PUBLICATIONS

Oksenberg, Arie and Donald Silverberg, *The Effect of Body Posture on Sleep-Related Breathing Disorders: Facts and Therapeutic Implications*, Sleep Medicine Reviews, vol. 2, No. 3, 139-162 (1998) (25 pages).

Oksenberg, Arie, et al., *Positional Therapy for Obstructive Sleep Apnea Patients: A 6-Month Follow-Up Study*, Laryngoscope 116, Nov. 2006, 1995-2000 (6 pages).

Oksenberg, Arie, et al., *REM-Related Obstructive Sleep Apnea: The Effect of Body Position*, Journal of Clinical Sleep Medicine, vol. 6, No. 4 (2010), 343-348 (6 pages).

Ozeke, Ozcan, et al., *Influence of the Right- Versus Left-Sided Sleeping Position on the Apnea-Hypopnea Index in Patients with Sleep Apnea*, Sleep Breath, published online Jun. 16, 2011 (5 pages).

Ozeke, Ozcan, et al., *Sleep Apnea, Heart Failure, and Sleep Position*, Sleep Breath, published online Nov. 9, 2011 (4 pages).

Permut, Irene, et al., *Comparison of Positional Therapy to CPAP in Patients with Positional Obstructive Sleep Apnea*, Journal of Clinical Sleep Medicine, vol. 6, No. 3 (2010), 238-243 (6 pages).

Author Unknown, *Positioning of Surgical Patients With Sleep Apnea*, ClinicalTrials.gov, http://clinicaltrials.gov/ct2/show/NCT02123238?term=apnea+and+position&rank=3 (2014) (5 pages).

Author Unknown, *Obstructive Sleep Apnea May Block the Path to a Positive Postoperative Outcome*, 2007 Pennsylvania Patient Safely Authority, reprinted from the PA-PSRS Patient Safety Advisory, vol. 4, No. 3 (Sep. 2007) (9 pages).

Proczko, Monika, et al., *STOP-Bang and the Effect on Patient Outcome and Length of Hospital Stay when Patients are not Using Continuous Positive Airway Pressure*, J Anesth, published online May 29, 2014 (7 pages).

Ramachandran, Satya Krishna, et al., *Derivation and Validation of a Simple Perioperative Sleep Apnea Prediction Score*, Society for Ambulatory Anesthesiology, vol. 110, No. 4 (Apr. 2010), 1007-1015 (9 pages).

Ravesloot, M.J.L. and N. de Vries, *Calculation of Surgical and Non-Surgical Efficacy for OSA /Reliable Calculation of the Efficacy of Non-Surgical and Surgical Treatment of Obstructive Sleep Apnea Revisted*, vol. 34, Issue 01 (2001) 105-110 (2 pages).

Ravesloot, M.J.L., et al., *The Undervalued Potential of Positional Therapy in Position-Dependent Snoring and Obstructive Sleep Apnea—A Review of the Literature*, Sleep Breath, published online Mar. 24, 2012 (11 pages).

Ravesloot, Madeline J.L., et al., *Treatment Adherence Should be Taken into Account when Reporting Treatment Outcomes in Obstructive Sleep Apnea*, Sleep Medicine, vol. 124, Issue 1 (Jan. 2014) 344-345 (3 pages).

Richardson, Annette and Anne Killen, *How Long do Patients Spend Weaning from CPAP in Critical Care?*, Intensive and Critical Care Nursing (2006) 22, 206-213 (8 pages).

Rosenberg, Russell and Paul Doghramji, *Optimal Treatment of Obstructive Sleep Apnea and Excessive Sleepiness*, Springer Healthcare Communication, published online Apr. 3, 2009, 295-312 (18 pages).

Rosenthal, Leon, *Got CPAP? Use it in the Hospital!*, Sleep Breath, published online Nov. 25, 2011 (4 pages).

Safiruddin, Faiza, et al., *Analysis of the Influence of Head Rotation During Drug-Induced Sleep Endoscopy in Obstructive Sleep Apnea*, Laryngoscope 124: Sep. 2014, 2195-2199 (5 pages).

Seet, Edwin and Frances Chung, *Obstructive Sleep Apnea: Preoperative Assessment*, Anesthesiology Clin 28 (2010) 199-215 (17 pages).

Seet, Edwin, et al., *Perioperative Clinical Pathways to Manage Sleep-Disordered Breathing*, Sleep Med Clin, 8 (2013) 105-120 (16 pages).

Sforza, Emilia, et al., *A 3-Year Longitudinal Study of Sleep Disordered Breathing in the Elderly*, European Respiratory Journal, vol. 40, No. 3 (2012) 665-672 (8 pages).

Sforza, E., et al., *Natural Evolution of Sleep Apnoea Syndrome: A Five Year Longitudinal Study*, European Respiratory Journal, 1994, 7, 1765-1770 (6 pages).

Shafazand, Shirin, *Perioperative Management of Obstructive Sleep Apnea: Ready for Prime Time?*, Cleveland Clinic Journal of Medicine, vol. 76, Supp. 4, Nov. 2009 (6 pages).

Siddiqui, Fouzia, et al. *Half of Patients with Obstructive Sleep Apnea have a Higher NREM AHI than REM AHI*, Sleep Medicine 7 (2006) 281-285 (5 pages).

Singh, M., et al., *Proportion of Surgical Patients with Undiagnosed Obstructive Sleep Apnoea*, British Journal of Anaesthesia 110 (4); 629-636 (2013) (8 pages).

Skinner, Margot A., et al., *Elevated Posture for the Management of Obstructive Sleep Apnea*, Sleep and Breathing, vol. 8, No. 4 (2004) 193-200 (10 pages).

Author Unknown, *There's More than One Way to Improve Nightime Breathing*, European Sleep Works, http://www.sleepworks.com/resource/medical-needs/sleep-apnea (2014) (3 pages).

Park, Steven V., *Sleep Apnea CPAP Compliance Craziness*, Doctor Steven Y_ Park, MD New York, NY Integrative Solutions for Obstructive Sleep Apnea, Upper Airway Resistance Syndrome, and Snoring (Nov. 10, 2009) (7 pages).

Monk, Timothy H., et al., *Measuring Sleep Habits Without Using a Diary: The Sleep Timing Questionnaire*, Sleep, vol. 26, No. 2 (2003) 208-212 (5 pages).

Sorscher, Adam J. and Evan M. Caruso, *Frequency of Provision of CPAP in the Inpatient Setting: An Observational Study*, Sleep Breath, published online Nov. 23, 2011 (6 pages).

Spurr, Kathy F., et al., *Prevalence of Unspecified Sleep Apnea and the use of Continuous Positive Airway Pressure in Hospitalized Patients, 2004 National Hospital Discharge Survey*, Sleep Breath (2008) 12:229-234 (8 pages).

Srijithesh PR, et al., *Positional Therapy for Obstructive Sleep Apnoea (Protocol)*, The Cochrane Library 2014, Issue 2 (11 pages).

Sundar, Eswar, et al., *Perioperative Screening for the Management of Patients with Obstructive Sleep Apnea*, JCOM, vol. 18, No. 9, Sep. 2011, 399-411 (13 pages).

Szollosi, Irene, et al., *Lateral Sleeping Position Reduces Severity of Central Sleep Apnea/Cheyne-Stokes Respiration*, Sleep, vol. 29, No. 8 (2006), 1045-1051 (7 pages).

Author Unknown, *A Promising Concept of Combination Therapy for Positional Obstructive Sleep Apnea*, Springer Link, http://link.springer.com/article/10.1007/s11325-014-1068-8, Oct. 2014 (4 pages).

Author Unknown, *Upper Airway Collapse During Drug Induced Sleep Endoscopy: Head Rotation in Supine Position Compared with Lateral Head and Truck Position*, Springer Link, http://link.springer.com/article/10.1007/s00405-014-3215-z, Aug. 2014 (4 pages).

Vasu, Tajender S., et al., *Obstructive Sleep Apnea Syndrome and Postoperative Complications*, Arch Otolaryngol Head Neck Surg, vol. 136, No. 10, Oct. 2010 (5 pages).

Matthews, Dan, *Mattresses—A Futile Weapon in the Fight Against Sleep Apnea*, http://www.danmatthewsdds.com/mattresses-%E2%80%93-futile-weapon-fight-sleep-apnea/ (2014) (1 page).

Marks, Steve, *Hospital Care of Patients with Sleep Apnea*, Areté Sleep Health, last modified on May 16, 2013 (63 pages).

Carlisle, Heather, *The Case for Capnography in Patients Receiving Opioids*, American Nurse Today, vol. 9, No. 9 (Sep. 2014) 22-27 (69 pages).

Gold, Jenny, *The Sleep Apnea Business Is Booming, and Insurers Aren't Happy*, NPR_ApnesvsInsurers.mht, (Jan. 16, 2012) (3 page).

Author unknown, *Sleep right, Sleep tight, Natural sleep before medicines, Sleep Diary*, www.nps.org.au/sleep, last modified Jul. 7, 2010 (4 pages).

Quan, S. F., *Evolution of OSA*, Thorax 1998; 53:532 (4 pages).

Maurer, J. T., et al., *Treatment of Obstructive Sleep Apnea with a New Vest Preventing the Supine Position*, Thieme-Connect (2003) (1 page).

Schreuder, K.E., *The Effect of Cervical Positioning on Benign Snoring by Means of a Custom-Fitted Pillow*, Centre for Sleep and Wake Disorders Kempenhaeghe, 5591 Ve Heeze, the Netherlands, last modified Dec. 1, 2011 (4 pages).

Chung, Frances, *Semi-up Right Position Study*, Clinical Trials.gov, last updated May 28, 2014 (5 pages).

(56) References Cited

OTHER PUBLICATIONS

Author Unknown, *National Sleep Foundation Sleep Diary*, National Sleep Foundation, last modified Apr. 18, 2003 (2 pages).

Takaoka, Shanon, CPAP Adherence, Is it too much "pressure"?, Feb. 7, 2007 (41 pages).

Seren, Suaf, *The Effect of Pure Prone Positioning Therapy for the Patients With Mild to Moderate Obstructive Sleep Apnea*, ClinicalTrials.gov, last updated Jun. 7, 2011 (4 pages).

Jackman, Shawn M. and Bruce Hubbert, *Riding the Wireless Wave (without wiping out)*, HIMSS12 Annual Conference & Exhibition, last modified Feb. 20, 2012 (133 pages).

De Vries, Nico and Madeline Ravesloot, *Apnea Calculator*, http://apneacalculator.com (2014) (2 pages).

Oexman, Robert, *Can a Mattress Really Impact Your Sleep?*, Huffpost Healthy Living, Posted Oct. 14, 2012, 10:00 a.m. (8 pages).

Palmer, Laura and Suzanne R. Morrison, *Obesity and Obstructive Sleep Apnea / Is there a limit for ambulatory surgery?*, OR Nurse Journal, Sep. 2014 (9 pages).

Oksenberg, Arie, *Are We Missing a Simple Treatment for Most Adults Sleep Apnea Patients? The Avoidance of the Supine Sleep Position*, ResearchGate.net, Aug. 12, 2014 (2 pages).

Author Unknown, *Obstructive Sleep Apnea (OSA), Care of Adult Patients*, St. Anthony Central Hospital Clinical Standards, Jul. 8, 2009 (9 pages).

Gross, Jeffrey B., *Practice Guidelines for the Perioperative Management of Patients with Obstructive Sleep Apnea: An Updated Report by the American Society of Anesthesiologists Task Force on Perioperative Management of Patients with Obstructive Sleep Apnea*, U.S. Department of Health & Human Services, updated on May 9, 2014 (13 pages).

O'Connor, Anahad, *Treating Sleep Apnea Without the Mask*, NYTimes.com, Apr. 9, 2012 (7 pages).

Stradling, J. R. and R. J. O. Davies, *Sleep 1: Obstructive Sleep Apnea/Hypopnoea Syndrome: Definitions, Epidemiology, and Natural History*, Thorax 2004;59:73-78 (6 pages).

Pyke, Josh, et al, *Continuous Pulse Oximetry Monitoring in the Inpatient Population*, Patient Safety & Quality Healthcare, May/Jun. 2009 (5 pages).

EP Search Report for Application No. EP 13 79 3571, dated Sep. 8, 2015 (9 pages).

Service Manual—"TotalCare® Bed System" from Hill-Rom, Product No. P1900, MAN112 Rev 7, by Hill-Rom Services, Inc. (2007) (1105 pages).

User Manual—"TotalCare® Bed System" from Hill-Rom, Product No. P1900, USR042 REV11, by Hill-Rom Services, Inc. (2009) (112 pages).

SleepEducation-Blog, "Positional therapy harness helps reduce sleep apnea for some," www.sleepeducation.com, posted Friday, Jun. 18, 2010 (7 pages).

SPANAmerica: PressureGuard® Turn Select®, www.archive.org/web/20090201172625/http://spanamerica.com/turn_select.php; Aug. 18, 2014 (2 pages).

PCT Search Report and Written Opinion for PCT/US2014/18033, completed Aug. 18, 2014 (17 pages).

PCT Search Report for PC5T/US2013/042313, completed Dec. 6, 2013 (4 pages).

Japanese Office Action for Japanese Patent Application No. 2017-073542 dated Jan. 7, 2018 and its English translation; 11 pages.

Japanese Patent Application Publication No. JP 2011-143237A dated Jul. 28, 2011 and its machine-generated English translation; 34 pages.

PCT Patent Application Publication No. WO 2013/031504 A1 published on Mar. 7, 2018 and the English translation of the Abstract only; 63 pages.

Extended European Patent Search Report for European Patent Application No. 19182070.3 dated Oct. 14, 2019 (9 pages).

\* cited by examiner

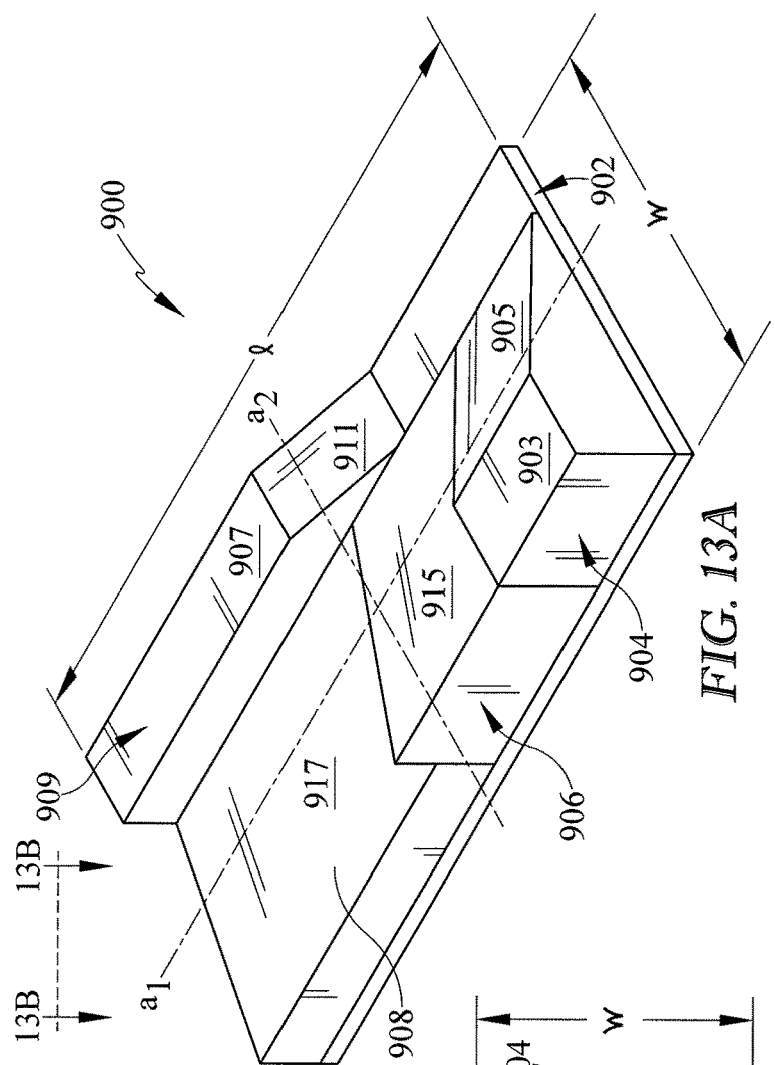
FIG. 13A
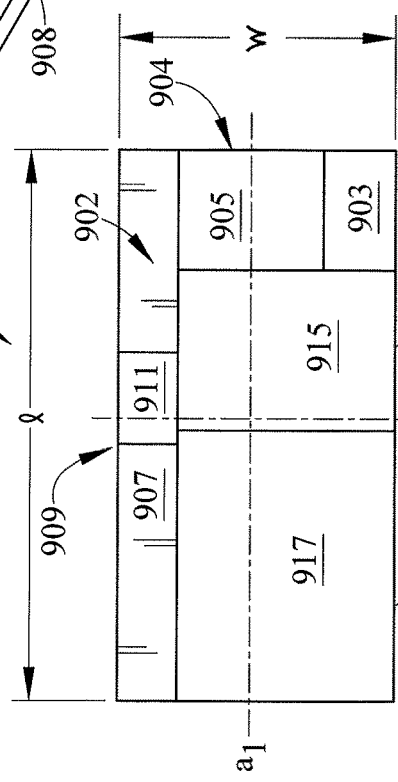
FIG. 13B
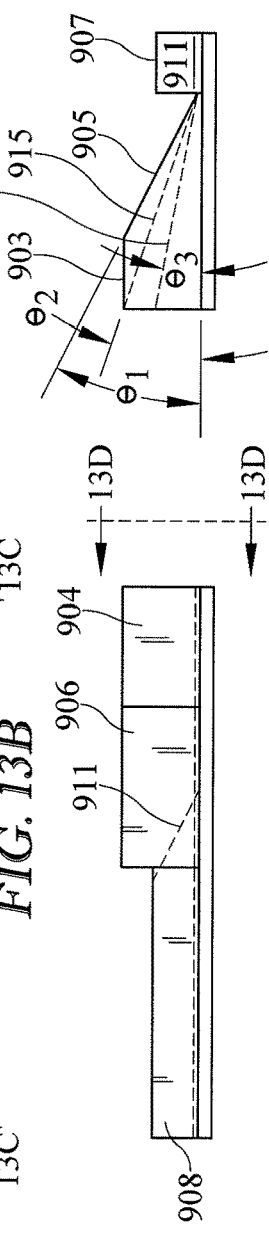
FIG. 13C
FIG. 13D

DYNAMIC APNEA THERAPY SURFACE

The present application is a divisional of U.S. application Ser. No. 14/848,513, filed Sep. 9, 2015, now U.S. Pat. No. 10,292,881, which claims the benefit, under 35 U.S.C. § 119(e), of U.S. Provisional Application No. 62/073,565, filed Oct. 31, 2014, and each of which is hereby incorporated by reference herein in its entirety.

BACKGROUND

This disclosure relates generally to dynamic person support surfaces, devices, systems, and methods configured to provide apnea therapy and/or therapy for other disorders.

SUMMARY

The present application discloses one or more of the features recited in the appended claims and/or the following features which, alone or in any combination, may comprise patentable subject matter:

According to the present disclosure, a dynamic person support system may include a person support surface that may have a pair of laterally spaced support segments. At least one of the support segments may include a lateral rotation apparatus. The lateral rotation apparatus may have a plurality of independently rotatable longitudinally arranged support planes and a lateral rotation actuator that may be operably coupled to one or more of the support planes. A first occupant sensor may be coupled to the support segment comprising the lateral rotation apparatus. A second occupant sensor may be coupled to the other support segment. A control unit may include a processor and a non-transitory machine readable storage medium that may have a dynamic therapy routine. The dynamic therapy routine may include instructions executable by the processor to cause the control unit to control the operation of the lateral rotation apparatus by: with the first occupant sensor, detecting a state of a first human subject on the support segment comprising the lateral rotation apparatus; with the second occupant sensor, detecting a state of a second human subject on the other support segment; and in response to the detected state of the first human subject and the detected state of the second human subject, controlling the lateral rotation actuator of the lateral rotation apparatus.

In some embodiments, the lateral rotation actuator may include an electromechanical device configured to drive lateral rotation of the independently rotatable support planes. Alternatively or additionally, the lateral rotation actuator may include a plurality of inflatable bladders supporting the independently rotatable support planes and an air supply operably coupled to the inflatable bladders. The second occupant sensor may be configured to detect a sleep state of the second human subject and the control unit may be configured to delay operation of the lateral rotation actuator until the second human subject is detected as being asleep.

In some embodiments, the first occupant sensor may be configured to detect a position of the first human subject relative to the support segment comprising the lateral rotation apparatus and the control unit may be configured to delay operation of the lateral rotation actuator if the detected position of the first human subject is not substantially on the support segment comprising the lateral rotation apparatus. If desired, the control unit may be configured to control the lateral rotation apparatus based on a combination of criteria including at least one criterion relating to the first human subject and at least one criterion relating to the second human subject. The control unit maybe configured to delay operation of the actuator until both the first human subject and the second human subject are detected as being asleep.

Further according to the present disclosure, a dynamic person support system may include a person support surface and a lateral rotation apparatus that may be coupled to the person support surface. The lateral rotation apparatus may include a plurality of independently rotatable longitudinally arranged support planes and a lateral rotation actuator operably coupled to one or more of the support planes. A control unit may include a processor and a non-transitory machine readable storage medium that may have a dynamic therapy routine. The dynamic therapy routine may include instructions that may be executable by the processor to cause the control unit to control the operation of the lateral rotation apparatus by: determining a maximum supine position duration; monitoring the actual supine position duration of a human subject positioned on the person support apparatus; and controlling the lateral rotation actuator to maintain the actual supine position duration below the maximum supine position duration.

In some embodiments, the lateral rotation actuator may include an electromechanical device configured to drive lateral rotation of the independently rotatable support planes. Alternatively or additionally, the lateral rotation actuator may include a plurality of inflatable bladders supporting the independently rotatable support planes and an air supply operably coupled to the inflatable bladders.

The control unit may be configured to compute the maximum supine position duration as a function of an apnea-hypopnea index (AHI) value of the monitored human subject. The control unit may be configured to compute the maximum supine position duration based on a first apnea-hypopnea index (AHI) value and a second AHI value. For example, the first AHI value may be determined while the human subject is in a supine position and the second AHI value may be determined while the human subject is in a non-supine position.

In some embodiments, the dynamic person support system may include a sensor in communication with the control unit. The control unit may be configured to receive a sensed value from the sensor and determine the maximum supine position duration based on the sensed value. The sensed value may be indicative of an apnea-hypopnea index (AHI) of the monitored human subject. Alternatively or additionally, the sensed value may be indicative of a sleep state of the monitored human subject. The control unit may be configured to adjust the maximum supine position duration in response to the sensed value. Optionally, the control unit may be configured to increase the maximum supine position duration in response to the sensed value being below a threshold value. Further optionally, the control unit may be configured to decrease the maximum supine position duration in response to the sensed value being above a second threshold value.

According to another aspect of the present disclosure, a lateral rotation apparatus may include a person support surface that may have head, torso and leg segments each of which may have an independently rotatable person support plane. A lateral rotation actuator may be operable to rotate the head segment to a head tilt angle in the range of about 7 to about 30 degrees relative to a horizontal support plane and to rotate the torso segment to a torso tilt angle that is within a range of about 5 degrees to about 10 degrees less than the head tilt angle.

In some embodiments, the lateral rotation actuator may include a plurality of inflatable bladders, and each person support plane may be supported by an inflatable bladder. Alternatively or additionally, the lateral rotation actuator may include an electromechanical device. The lateral rotation actuator may be operable to rotate the torso segment to a torso tilt angle in the range of about zero to about 25 degrees. The lateral rotation actuator may be operable to rotate the head segment to a head tilt angle in the range of about 10 to about 15 degrees. The lateral rotation actuator may be operable to rotate the torso segment to a torso tilt angle in the range of about 5 to about 10 degrees. The lateral rotation actuator may be operable to rotate the leg segment to a leg tilt angle in the range of about 0 to about 5 degrees.

The lateral rotation apparatus may include a control unit that may control inflation of the bladders to maintain a differential between the head tilt angle and the torso tilt angle. For example, the differential may be in the range of about 5 to about 10 degrees. The torso segment may be longitudinally longer than the head segment and the leg segment may be longitudinally longer than the torso segment. For example, the head segment may have a longitudinal length of about 16 inches, the torso segment may have a longitudinal length of about 24 inches, and the leg segment may have a longitudinal length of about 40 inches.

In some embodiments, the person support surface may include a support material having a density and the head tilt angle may be a function of the density of the support material. Alternatively or additionally, the torso tilt angle may be a function of the density of the support material.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

Referring now to the illustrative examples in the drawings, wherein like numerals represent the same or similar elements throughout:

FIG. 13A is a simplified perspective view of at least one embodiment of a dynamic therapy surface as disclosed herein;

FIG. 13B is a simplified top view of the dynamic therapy surface of FIG. 13A, looking in the direction labeled 13B in FIG. 13A;

FIG. 13C is a simplified longitudinal side view (viewed along the longer side) of the dynamic therapy surface of FIG. 13A, looking in the direction labeled 13C in FIG. 13B;

FIG. 13D is a simplified lateral side view (viewed along the shorter side, or end) of the dynamic therapy surface of FIG. 13A, looking in the direction labeled 13D in FIG. 13C;

DETAILED DESCRIPTION

Figure 1:
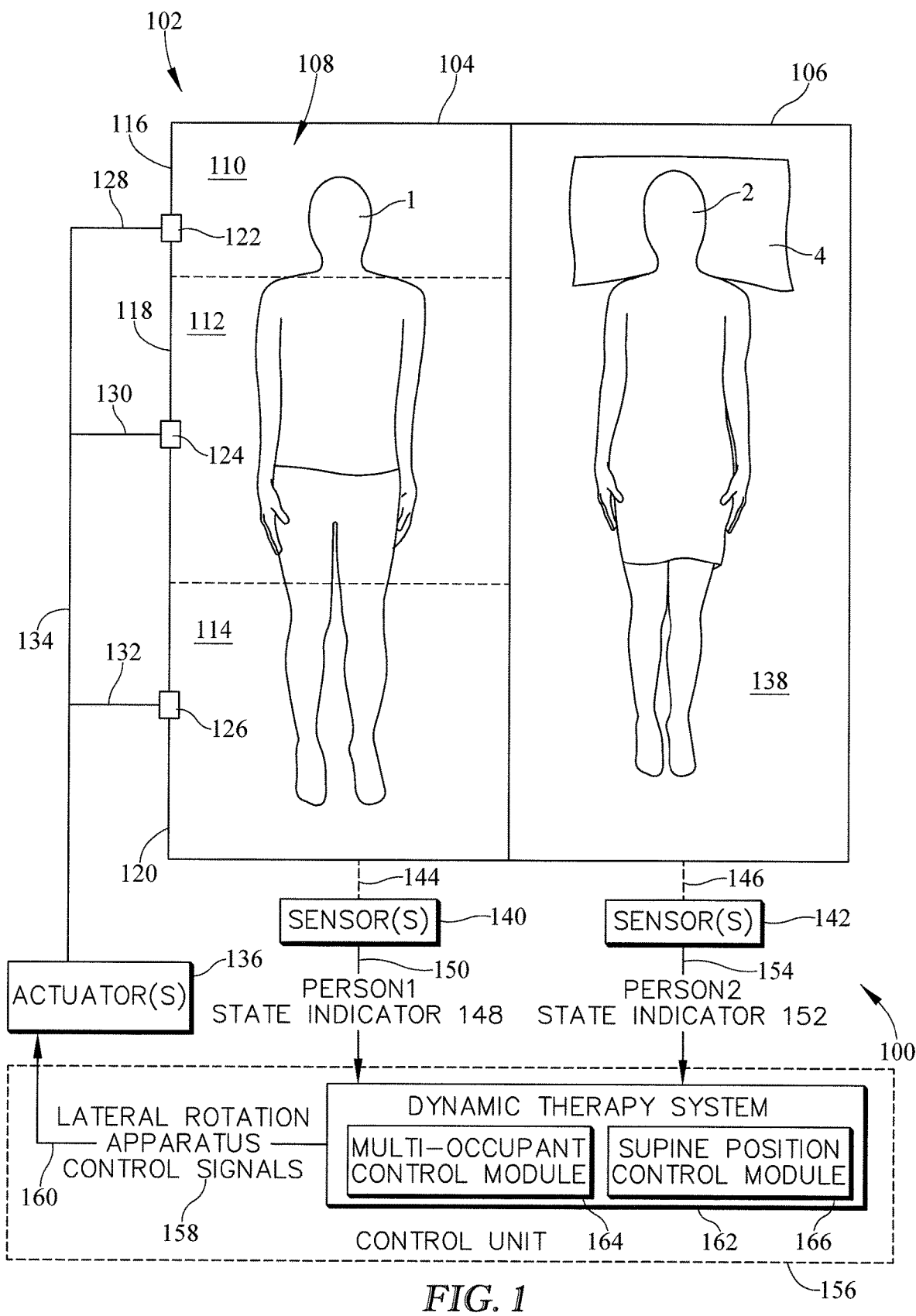
FIG. 1 is a simplified schematic view of at least one embodiment of a person support system, including a simplified top view of a dynamic therapy surface configured for multiple occupants.

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

Technologies for laterally rotating a support surface as a treatment or therapy for sleep apnea and/or other disorders are disclosed in PCT Application No. PCT/US2013/042313 filed May 22, 2013; PCT Application No. PCT/US2014/018033, filed Feb. 24, 2014; U.S. Utility application Ser. No.

14/454,961 filed Aug. 8, 2014; and U.S. Design Pat. No. 29/498,872, each of which is incorporated herein by this reference. These and other similar technologies can be applied to circumstances in which multiple persons utilize a common sleep surface. These technologies can be improved by controlling a common support surface based on inputs from both the apnea sufferer and a second individual positioned on the common support surface. Alternatively or in addition, these technologies can be improved by controlling the support surface based on a maximum allowable supine sleep position duration. For example, whereas current approaches may strive to eliminate all supine sleep activities in order to reduce a person's apnea-hypopnea index (AHI) to below a threshold value), the control methods disclosed herein, which manage a dynamic sleep surface to a specified maximum supine sleep position duration value, can be applied to achieve that same goal with less aggressive therapy.

Figure 2:
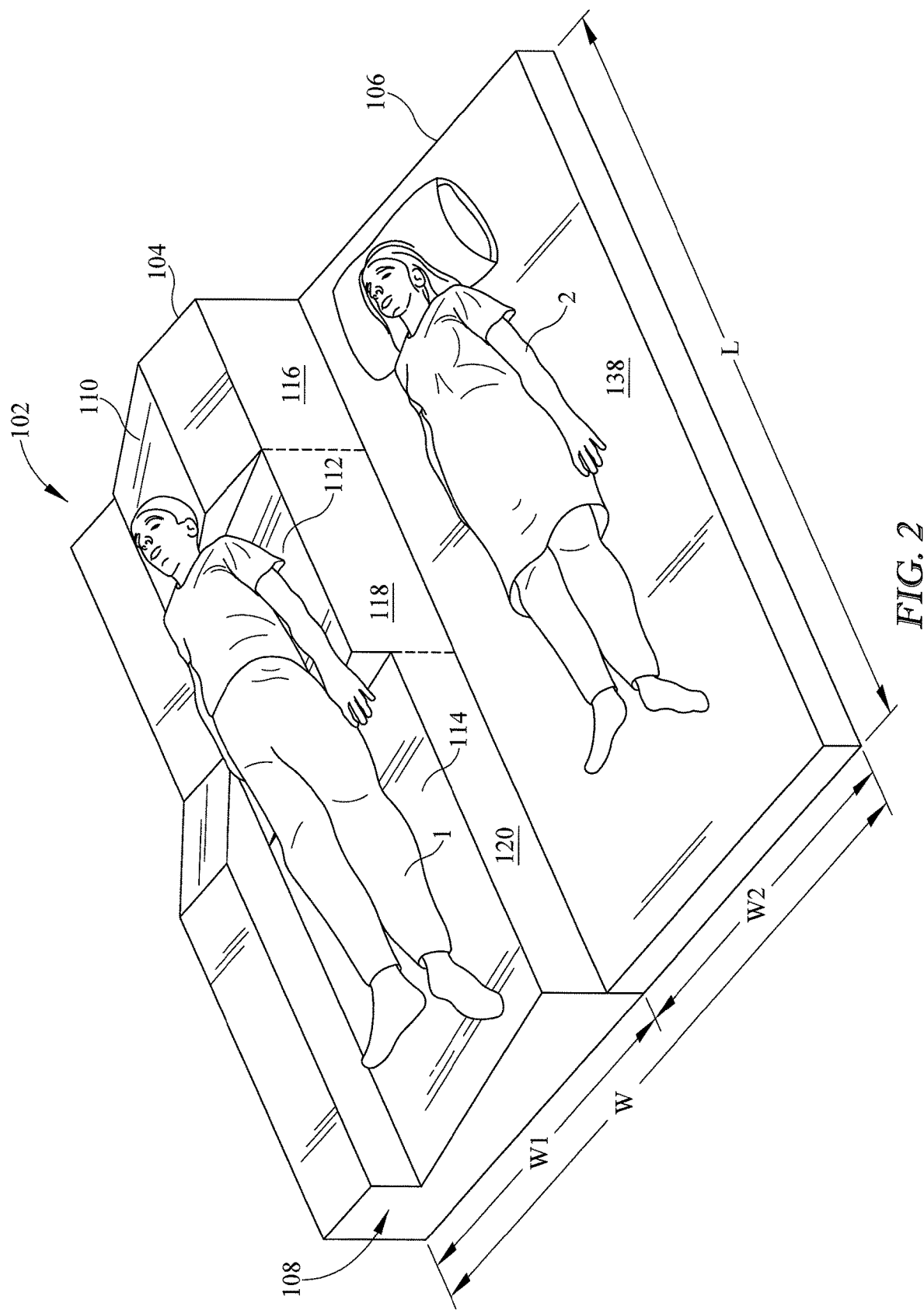
FIG. 2 is a simplified perspective view of at least one embodiment of the dynamic therapy surface of FIG. 1, showing at least one embodiment of a lateral rotation apparatus supporting one of the occupants in a therapy position on a segment of the dynamic therapy surface.
Figure 3:
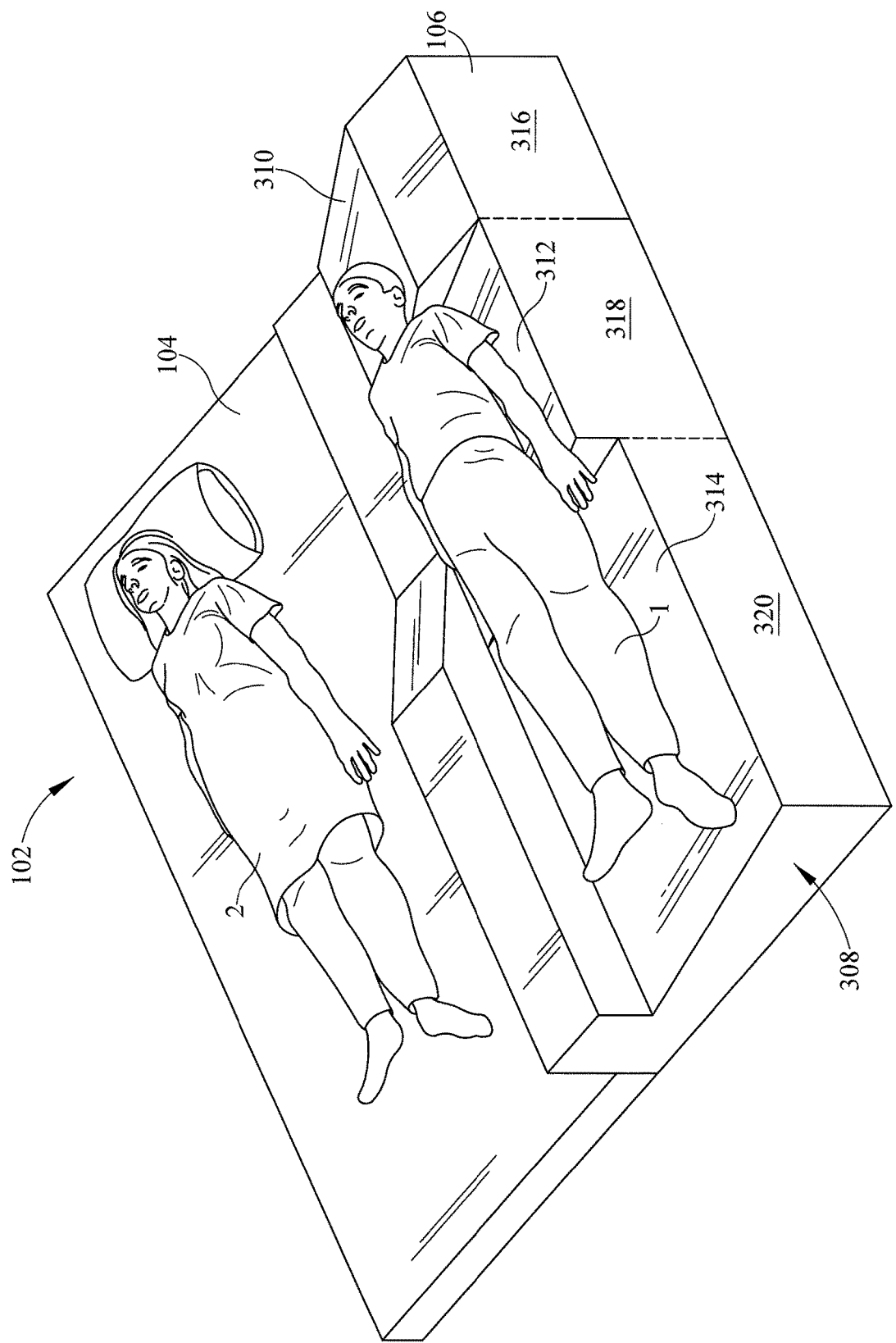
FIG. 3 is another simplified perspective view of at least one embodiment of the dynamic therapy surface of FIG. 1, showing at least one embodiment of the lateral rotation apparatus supporting the occupant in the therapy position on a different segment of the dynamic therapy surface.

Referring now to FIGS. 1-3, a person support system 100 includes a person support surface 102, a lateral rotation apparatus 108, and a control unit 156. A number of occupant sensors 140, 142 are in communication with the control unit 156 (e.g., by wired, wireless, optical, or other signal communication mechanism). The illustrative person support surface 102 includes a pair of laterally spaced support segments 104, 106, although other embodiments may only include a single support segment (e.g., support segment 104). At least one of the support segments 104, 106 is configured as or includes a lateral rotation apparatus 108. As described in more detail below, the illustrative lateral rotation apparatus 108 includes a number of different support sections, including independently rotatable longitudinally arranged support planes 110, 112, 114 and lateral rotation sections 116, 118, 120. The lateral rotation sections 116, 118, 120 may be embodied as, for example, a non-inflatable support material, such as foam, or as inflatable bladders, or as a combination of a non-inflatable support material and bladders. FIGS. 10-12 and 13A-13D, described below, show illustrative embodiments of a person support surface 102 and lateral rotation sections 116, 118, 120.

The lateral rotation sections 116, 118, 120 are coupled to the support planes 110, 112, 114 by linkages 122, 124, 126, 128, 130, 132, 134, and one or more lateral rotation actuators 136. The lateral rotation actuators 136 drive lateral rotation of the support planes 110, 112, 114. The operation of the lateral rotation actuators 136 is dynamically controlled by the control unit 156, as described in more detail below.

In some embodiments, the lateral rotation actuators 136 are powered (e.g., electronic or electromechanical) devices, such as electric motors or linear actuators, and the linkages 122, 124, 126, 128, 130, 132, 134 include, e.g., drive arms or output shafts. In other embodiments, the support sections 116, 118, 120 each include one or more inflatable bladders, which support the support planes 110, 112, 114, respectively; the actuator 136 is an air supply unit, and the linkages 122, 124, 126, 128, 130, 132, 134 are pneumatic couplings including, e.g., air supply lines 128, 130, 132, 134 and valves 122, 124, 126. In "air bladder" embodiments, the bladders 116, 118, 120 are selectively inflated and deflated by the air supply 136 via the pneumatic couplings 122, 124, 126, 128, 130, 132, 134. The inflation and deflation of the bladders 116, 118, 120 is dynamically controlled by the control unit 156 operating the air supply 136 to supply air to or extract air from the bladders 116, 118, 120, as the case may be, in response to inputs from the occupant sensors 140, 142. The air supply 136 delivers air to the bladders 116, 118, 120 via one or more supply lines 128, 130, 132, 134 and valves 122, 124, 126. The air supply 136 may be embodied as, e.g., a blower, a compressor, or a vacuum/blower. Any suitable configuration of air supply lines and valves may be used. For example, multiple air supply lines may be connected to a valve manifold, in some embodiments. The valves 122, 124, 126 may be electronically controlled, e.g., by the control unit 156, in some embodiments. The actuator(s) can be configured to operate slowly and quietly, in order to minimize disruption to any occupant on the bed. For instance, the actuator 136's rate of change may be controlled by algorithms taking inputs from one or more of the sensors 140, 142 or other sensors.

Illustratively, the support segment 106 is embodied as a support section having a single support plane 138. In other embodiments, the support segment 106 may include multiple different support planes. For example, the support segment 106 may be embodied in a similar fashion to the support segment 104 and may include another lateral rotation apparatus or another type of therapy device.

In some embodiments, the sensor 140 is operably coupled to the support segment 104 by a coupler 144, and the sensor 142 is operably coupled to the support segment 106 by a coupler 146. Each or either of the sensors 140, 142 may be attached to a surface of the support segment 104, 106, respectively, embedded in the respective support segment 104, 106, or mounted to a frame or deck that supports the support segment 104, 106, (e.g., a frame or deck that is similar or analogous to the frame 80 or the deck 86 shown in FIG. 8). As such, the couplers 144, 146 may be embodied as, for example, screws, rivets, stitching, brackets, adhesive, or other suitable fasteners. Alternatively, one or more of the sensors 140, 142 may simply rest on a frame or deck surface, within a pocket or enclosure of the support segment 104, 106, etc. Still further, each or any of the sensors 140, 142 may be in communication with the control unit 156 but not directly coupled to the support surface 102. For instance, any of the sensors 140, 142 may be embodied in a mobile or wearable computing device, such as a smart phone, a tablet computer, a smart watch, smart jewelry (e.g., a smart bracelet), smart glasses, or as a wearable sensor, such as a smart textile, a "clip-on" sensor, or a body-worn sensor (e.g., an electrode). As such, each or any of the sensors 140, 142 may be associated with a person using the support surface 102 (e.g., person 1 or person), rather than being directly associated with the support surface 102 or a section thereof. In these embodiments, the links 144, 146 may represent logical associations of sensors 140, 142 with persons carrying the sensors 140, 142, rather than physical connections with the support surface 102. For example, a sensor identifier may be associated with a person by a user identifier (user ID), and the data identifying persons and associated sensors may be stored in memory of the sensor 140, 142 or another device (e.g., in an electronic file, mapping table, or database). Thus, when a sensor 140, 142 communicates state indicators 148, 152 to the control unit 156, the sensor communications may include the sensed information as well as the user ID of the person with whom the sensor 140, 142 is associated.

Each or any of the sensors 140, 142 may be embodied as a single sensor or an array or combination of multiple sensors (e.g., a pressure map). The sensors 140, 142 may be of the same type or of different types. The sensors 140, 142 may each be embodied as any suitable type of device that is capable of sensing an indicator of a state of a person positioned on the person support surface 102, and may include, e.g., a pressure sensor, a force sensor, a temperature sensor, an accelerometer, an inclinometer, a physiological or vital signs sensor, a microphone or other sound detector, a sleep sensor (e.g., any type of sensor that can detect an indicator of a person's sleep, including any of the foregoing), an array of any of the foregoing types of sensors, or any combination of any of the foregoing types of sensors and/or others sensors.

In operation, the sensor 140 detects state information about a person 1 situated on the support segment 104, and the sensor 142 detects state information about a person 2 situated on the support segment 106 (illustratively, with head supported by a pillow 4), over a fixed or variable time interval. Each of the respective person 1 and person 2 state information may include, for example, an indication of: whether the person is awake or asleep, the particular stage of the person's sleep (e.g., rapid eye movement (REM) phase or not), the person's position relative to the support segment 104 or 106 (e.g., in order for the control unit 156 to determine whether the person in a proper position for a therapy to be performed), the person's activity level, one or more physiological parameters of the person (e.g., blood pressure, blood oxygen saturation, heart rate, respiration rate, etc.) and/or other person state indicators. The system 100 can be programmed to automatically disable or terminate the rotation (e.g., apnea therapy) if the system 100 detects an adverse condition. Alternatively or in addition, the system 100 can terminate or suspend the rotation (e.g., apnea therapy) by a manual override (such as a switch).

Figure 4:
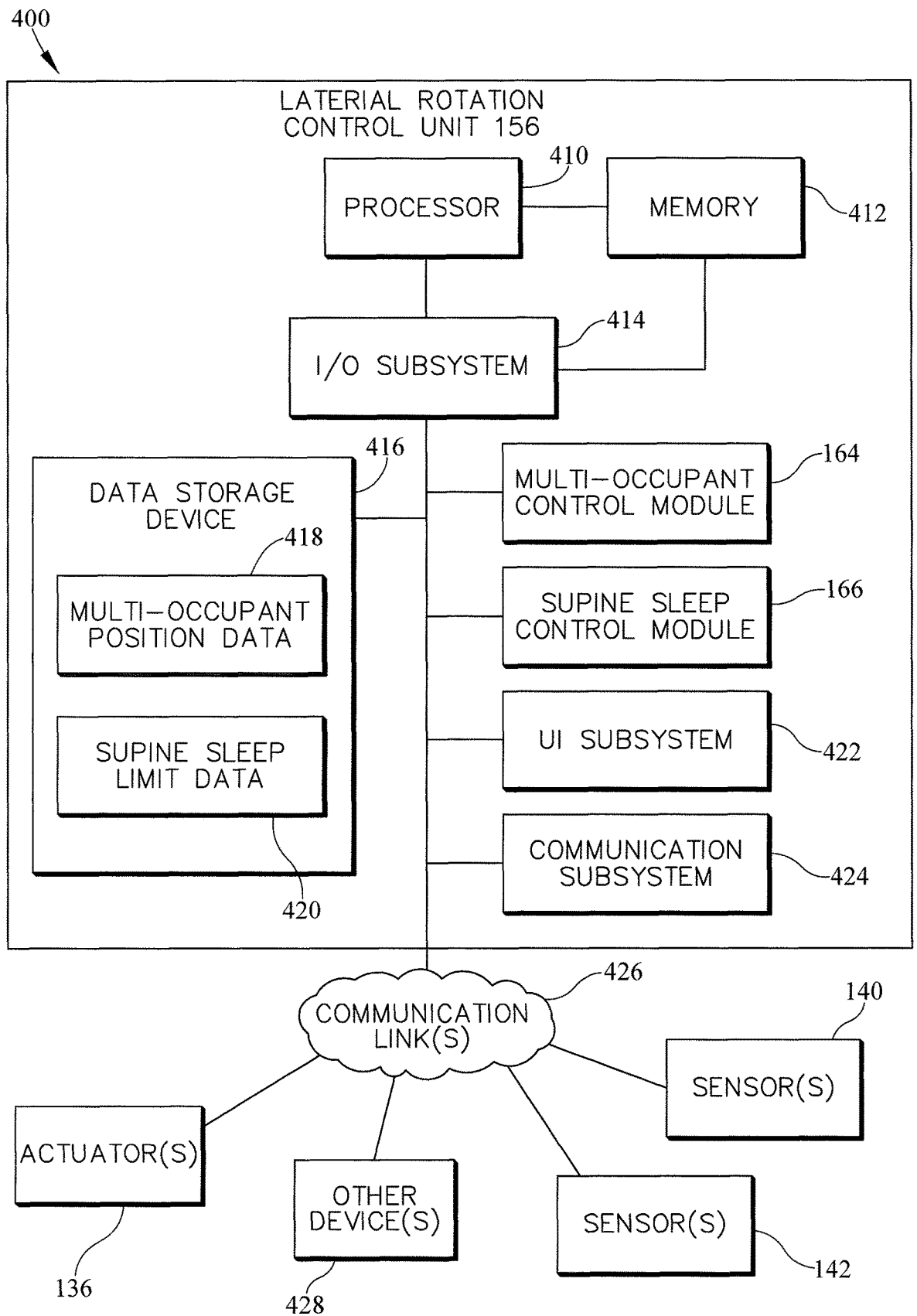
FIG. 4 is a simplified block diagram of at least one embodiment of the control unit and other components of the person support system of FIG. 1.

The control unit 156 receives person1 state indicators 148 from time to time from the sensor 140, and receives person2 state indicators 152 from time to time from the sensor 142, by way of suitable communication links 150, 154 as shown in FIG. 4, described below. The control unit 156 includes electrical circuitry and/or computer components, as shown in FIG. 4, which are configured as a dynamic therapy system 162. Aspects of the dynamic therapy system 162 may be embodied in a similar fashion to the computer system shown in FIGS. 14-15, described below.

The illustrative dynamic therapy system 162 includes a multi-occupant control module 164 and a supine position control module 166. The modules 162, 164 may each be embodied as computer hardware, software, firmware, or a combination thereof. The multi-occupant control module 164 causes the control unit 156 to read and analyze the person1 state indicator 148 and the person2 state indicator 152, execute control algorithms, and issue lateral rotation apparatus control signals 158 from time to time based on a combination of the person1 and person2 state indicators 148, 152. The supine position control module 166 causes the control unit 156 to read and analyze at least the person1 state indicator 148, execute control algorithms, and issue lateral rotation apparatus control signals 158 from time to time based on at least the person1 state indicator 148 in combination with maximum supine position duration information stored in e.g., a memory accessible by the control unit 156.

The control unit 156 transmits the lateral rotation apparatus control signals 158 to the actuator 136 via a communication link 160, to activate or deactivate the actuator 136. For example, the control signals 158 may cause a motor to drive mechanical elements (e.g., linkages 122, 124, 126, 128, 130, 132, 134) to rotate a support section 116, 118, 120, or may cause an air supply to increase or decrease a supply of air to one or more of the bladders 116, 118, 120 in response to the lateral rotation apparatus control signals 158. For example, the control signals 158 may cause one or more of the actuator(s) 136 to turn on or off, increase or decrease a power level, or supply positive or negative pressure to one or more of the support sections or bladders 116, 118, 120. Features of the multi-occupant control module 164 and the supine position control module 166 are described in more detail below, with reference to FIGS. 5 and 6, respectively.

In FIG. 2, the person support surface 102 is shown in a state in which the lateral rotation apparatus 108 of the support segment 104 is activated to place the person 1 in a non-supine position on the support segment 104. At the same time, the support segment 106 remains in a flat position, allowing the person 2 to remain in a supine position. The position of the person 1 in FIG. 2 is considered "non-supine" in that while the person 1 is laying on his back, the head, torso, and legs are rotated at different angles, so that the person 1 is not laying flat.

Relative dimensions of the person support surface 102 are also shown in FIG. 2. The support segment 104 has a width W1, and the support segment 106 has a width W2. The widths W1, W2 may be the same or different. The width W is greater than either the width W1 or the width W2, and may equal the sum of W1 plus W2. The person support surface 102 has a length L, which is greater than either of W1 and W2 and typically greater than the width W. Illustratively, both of the support segments 104, 106 have the same length L, but may have different lengths, in other embodiments. It should be noted that the support segments 104, 106 can be subcomponents of the same support surface (e.g., a double bed, with one mattress having two lateral sides), such that both person 1 and person 2 are on the same surface), or the support segments 104, 106 may be separate surfaces (e.g., two mattresses supported by a common support frame). Each or either of the support segments 104, 106 may be equipped with a lateral rotation apparatus 108. For example, both persons 1 and 2 could be apnea sufferers and thus both sides of the person support surface 102 would be equipped with a lateral rotation apparatus 108. In such embodiments, the operation of both of the lateral rotation apparatuses can be coordinated by the control unit 156.

In FIG. 3, the person support surface 102 is shown in a configuration in which a lateral rotation apparatus 308 is part of the support segment 106. As such, either or both support segments 104, 106 may be configured with a lateral rotation apparatus 108, 308. As shown in FIG. 3, the lateral rotation apparatus 308 includes support planes 310, 312, 314 and support sections (e.g., foam and/or bladders) 316, 318, 320. The illustrative lateral rotation apparatus 308 is analogous to the lateral rotation apparatus 108. As such the support planes 310, 312, 314 may be embodied in a similar manner as the support planes 110, 112, 114, and the support sections 316, 318, 320 may be embodied in a similar manner as the support sections 116, 118, 120, described above. In other embodiments, the components of the person support surface 102 and more particularly, the lateral rotation apparatus 108, 308, may include other components and/or other configurations of the same components. For instance, portions of the person support surface 102, and more generally the person support system 100, may include one or more of the features shown in FIGS. 7-12 and 13A-13D.

The illustrative lateral rotation apparatus 108 includes a support surface comprising head, torso and leg segments each having an independently rotatable person support plane 110, 112, 114; and corresponding support sections 116, 118, 120, which support each person support plane. The support sections 116, 118 120 may be embodied as different subsections of a common support surface or as separate support surfaces. Further, the support sections 116, 118, 120 need not be independent from one another. For example, the support sections 116, 118, 120 may share a common layer, with one or more additional layers above or below the support sections 116, 118, 120.

In some embodiments, the ranges of lateral tilt angles that the support planes 110, 112, 114 can assume are as follows. The actuator 136 may be operable to rotate the support plane 110 (e.g., head segment) to a head tilt angle in the range of about 7 to about 30 degrees relative to a horizontal support plane; and the actuator 136 may be operable to rotate to rotate the support plane 112 (e.g., torso segment) to a torso tilt angle that is within a range of about 5 degrees to about 10 degrees less than the head tilt angle. The support section 118 may be configured to rotate the support plane 112 (e.g., torso segment) to a torso tilt angle in the range of about zero to about 25 degrees. The support section 116 may be configured to rotate the support plane 110 (e.g., head segment) to a head tilt angle in the range of about 10 to about 15 degrees. The support section 118 may be configured to rotate the support plane 112 (e.g., torso segment) to a torso tilt angle in the range of about 5 to about 10 degrees. The support section 120 may be inflatable to rotate the support plane 114 (e.g., leg segment) to a leg tilt angle in the range of about 0 to about 5 degrees. In some embodiments, the lateral rotation apparatus 108 is configured to position/rotate all of the support planes 110, 112, 114 to the same angle (e.g., all of the support planes 110,112, 114 rotated to an angle of about 10 degrees). In some embodiments, the head, torso, and/or leg tilt angles may be computed in order to allow for indentation of the support surface 102 underneath body parts such as shoulders, arms and hips (e.g., so that the patient's shoulder, arm, or hip can rest comfortably underneath the body).

The control unit 156 (e.g., a bed or mattress controller) may control inflation of the bladder 116 and the bladder 118 to maintain a differential between the head tilt angle and the torso tilt angle that is in the range of about 5 to about 10 degrees. In other words, the control unit 156 may coordinate lateral rotation (e.g., lateral tilt) angle changes of the support planes 110, 112 so that the differential between the two angles does not exceed a desired amount.

In some embodiments, the support plane 112 (e.g., torso segment) may be longitudinally longer than the support plane 110 (e.g., head segment), and the support plane 114 (e.g., leg segment) may be longitudinally longer than the support plane 112 (e.g., torso segment). For example, the support plane 110 (e.g., head segment) may have a longitudinal length in the range of about 16 inches; the support plane 112 (e.g., the torso segment) may have a longitudinal length in the range of about 24 inches; and the support plane 114 (e.g., the leg segment) may have a longitudinal length in the range of about 40 inches.

Portions of the person support surface 102 may be made of a support material that has a density, such as a foam material. The head tilt angle may be configured as a function of the density of the support material. Either or both of the torso tilt angle and the leg tilt angle may also be configured as a function of the density of the support material. In other words, the head, torso and leg tilt angles may vary according to the density of the material used to build the person support surface 102 or person-supporting portions thereof. Alternatively or in addition, the head, torso, and leg tilt angles may be configured as a function of an occupant's body weight and/or as a function of the morphology of the person's body interfacing with the person support surface 102. Thus, the occupant's body weight can be an additional input for the calculation of the tilt angle. In addition, a sensor that measures the actual tilt angle of the person's body can be used in a closed-loop system to determine the optimum tilt angles for the support planes 110, 112, 114.

Referring now to FIG. 4, a simplified block diagram of an embodiment 400 of the person support system 100 is shown. The person support system 400 includes the lateral rotation control unit 156, one or more communication links 426, the air supply 136, the sensors 140, 142, and one or more other devices 428. While the illustrative embodiment 400 is shown as involving multiple components and devices, it should be understood that the person support system 400 may constitute a single device, alone or in combination with other devices. For example, the air supply 136 may be a component of the control unit 156, a component of the person support surface 102, or a separate component. Each or any of the components 156, 140, 142, 428, 136 may be in communication with one another via one or more of the communication links 426.

In some embodiments, portions of the system 400 may be incorporated into other systems or computer applications. Such applications or systems may include, for example, commercial off the shelf (COTS) or custom-developed devices or systems. As used herein, "module" or "component" may refer to, among other things, any type of computer program or group of computer programs, whether implemented in software, hardware, firmware, or a combination thereof, and includes self-contained, vertical, and/or shrink-wrapped applications, distributed and cloud-based applications, and/or others.

The illustrative lateral rotation control unit 156 includes at least one processor 410 (e.g. a microprocessor, microcontroller, digital signal processor, etc.), memory 412, and an input/output (I/O) subsystem 414. The control unit 156 may be embodied as any type of computing device capable of performing the functions described herein. Although not specifically shown, it should be understood that the I/O subsystem 414 can include, among other things, an I/O controller, a memory controller, and one or more I/O ports. The processor 410 and the I/O subsystem 414 are communicatively coupled to the memory 412. The memory 412 may be embodied as any type of suitable computer memory device, including fixed and/or removable memory devices (e.g., volatile memory such as a form of random access memory or a combination of random access memory and read-only memory, such as memory cards, e.g., SD cards, memory sticks, hard drives, and/or others).

The I/O subsystem 414 is communicatively coupled to a number of hardware, firmware, and/or software components, including the multi-occupant control module 164 and the supine position control module 166. The I/O subsystem 414 is also communicatively coupled to one or more data storage devices 418, a communication subsystem 424, and a user interface subsystem 422. The user interface subsystem 422 may include, for example, hardware or software buttons or actuators, a keypad, a display device, visual cue illuminators, and/or others.

The data storage device 416 is embodied as one or more machine readable storage media and may include one or more hard drives or other suitable data storage devices (e.g., flash memory, memory cards, memory sticks, and/or others). In some embodiments, portions of the system 400 containing data or stored information, e.g., multi-occupant position data 418, supine sleep limit data 420, and/or other data, reside at least temporarily in the data storage device 416. Portions of the system 400, e.g., multi-occupant position data 418, supine sleep limit data 420, and/or other data, may be copied to the memory 412 during operation of the control unit 156, for faster processing or other reasons.

The communication subsystem 424 communicatively couples the control unit 156 to one or more other devices, systems, or communication networks, e.g., a local area network, wide area network, personal cloud, enterprise cloud, public cloud, and/or the Internet, for example. Accordingly, the communication subsystem 424 may include a databus, datalink, one or more wired or wireless network interface software, firmware, or hardware, for example, as may be needed pursuant to the specifications and/or design of the particular embodiment of the control unit 156. The system 100 may also access data on a personal mobile device, where such data is either stored in the device memory or through its connection to the Internet, cloud, or other communication network. For example, a WIFI-enabled device such as a body weight scale or fitness tracker can send measured body weight data to an app on the mobile device. Such body weight data can be transmitted wirelessly to and used by the control unit 156 to, e.g., calculate the tilt angles of the support planes 110, 112, 114.

The other device(s) 428 may be embodied as any suitable type of computing device, electronic device, or electromechanical device capable of performing the functions described herein, such as any of the aforementioned types of devices or other electronic devices. For example, in some embodiments, a device 428 may operate a "back end" portion of the dynamic therapy system 162, by performing data storage or other operations of the control unit 156. In other embodiments, a device 428 may operate a "front end" portion of the dynamic therapy system 162. For instance, a front end portion may be embodied as an "app" that runs on a personal mobile electronic device, which enables user input to the dynamic therapy system 162 and display of output produced by the dynamic therapy system 162.

The system 400 may include other components, subcomponents, and devices not illustrated in FIG. 4 for clarity of the description. In general, the components of the system 40 are communicatively coupled as shown in FIG. 4 by one or more communication links 2048, e.g., signal paths, which may be embodied as any type of wired, optical, or wireless signal paths capable of facilitating communication between the respective devices and components, including direct connections, public and/or private network connections (e.g., Ethernet, Internet, etc.), or a combination thereof, and including short range (e.g., Near Field Communication) and longer range (e.g., Wi-Fi or cellular) wireless communication links.

Figure 5:
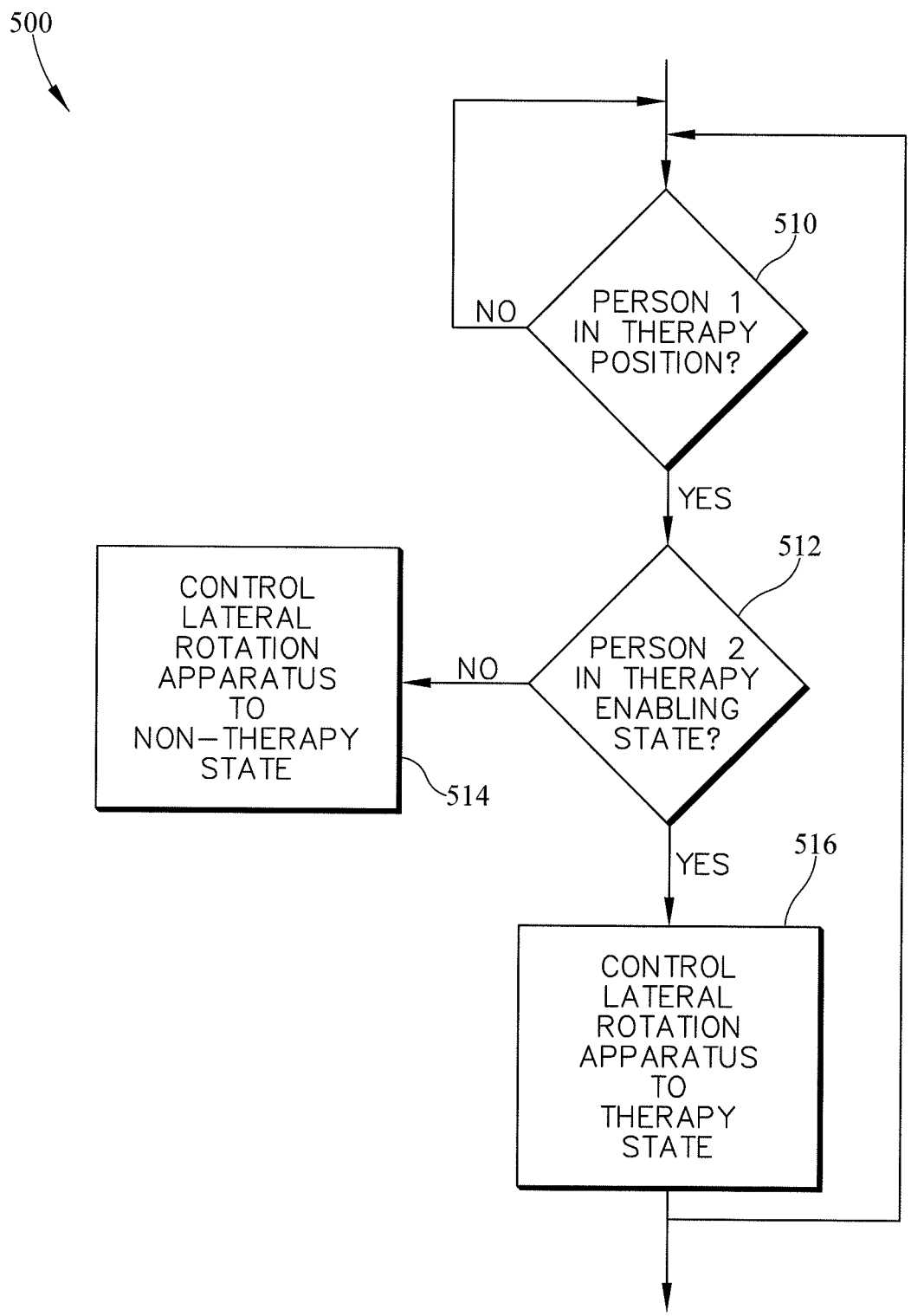
FIG. 5 is a simplified flow diagram of at least one embodiment of a method for controlling a lateral rotation apparatus such as the lateral rotation apparatus of FIG. 1 based on inputs relating to multiple occupants of a dynamic therapy surface such as the dynamic therapy surface of FIG. 1.

Referring now to FIG. 5, an example of a method 500 executable by one or more components of the person support system 100 (e.g., by the multi-occupant control module 164 of the control unit 156), is shown. The method 500 may be embodied as computerized programs, routines, logic and/or instructions, which may be embodied in hardware, software, firmware, or a combination thereof, of the system 100 and/or one or more other systems or devices in communication with the system 100. In block 510, the system 100 determines whether a "person 1" (e.g., a person needing apnea therapy or another type of therapy provided by the lateral rotation apparatus 108) is in position for the therapy to begin. To do this, the system 100 reads and analyzes data signals from an occupant sensor monitoring a portion of a person support surface that includes a lateral rotation apparatus (e.g., the support segment 104). The system 100 may compare the sensed data values to known values indicative of various patient positions, which may be determined based on experimentation and test results. In doing so, the system 100 may query a database or access a lookup table (e.g., multi-occupant data 418), and then perform a logical comparison of the current sensed value to one or more known values indicative of a person position relative to the support surface. For instance, the system 100 may determine from force sensor or pressure sensor readings that person 1 is laying down on the therapy-providing support segment. As another example, the system 100 may determine, based on one or more sensor inputs, that a substantial portion of person 1 is not positioned on the therapy-providing support segment. This may occur if person 1 is sitting on the edge of the person support surface or laying partially on the other lateral side of the person support surface (e.g., the support segment 106). The specific parameters for determining whether person 1 is in a therapy-enabling position may be selected according to the requirements of a particular design of the system 100. If the system 100 does not detect that person 1 is in a therapy-enabling position, the system 100 remains in block 510. If the system 100 detects that person 1 is in a therapy-enabling position, the system 100 proceeds to block 512.

In block 512, the system 100 determines whether a "person 2" is in a therapy-enabling state. The specific parameters for determining whether person 2 is in a therapy enabling state may be selected according to the requirements of a particular design of the system 100. For instance, the therapy enabling state may be defined as a sleep state, e.g., whether the person 2 is fully asleep, or in a REM state of sleep, or not yet asleep, or fully awake, or as an activity state, based on the person 2's level of motor activity in relation to the patient support surface. To determine whether person 2 is in a therapy-enabling state, the system 100 reads and analyzes data signals from an occupant sensor monitoring a portion of a person support surface that supports person 2 (e.g., the sensor 142). The system 100 may compare the sensed data values to known values indicative of various therapy-enabling states, which may be determined based on experimentation and test results. In doing so, the system 100 may query a database or access a lookup table (e.g., supine sleep limit data 420), and then perform a logical comparison of the current sensed value to one or more known values indicative of a desired therapy-enabling state. If the system 100 determines in block 512 that person 2 is not in a therapy-enabling state (e.g., person 2 is not yet asleep), the system 100 proceeds to block 514. If the system 100 determines in block 512 that person 2 is in a therapy-enabling state (e.g., person 2 is in a deep sleep and is therefore unlikely to be bothered by the therapy), the system 100 proceeds to block 516.

In block 514, the system 100 controls the lateral rotation apparatus to a non-therapy state. To do this, the system 100 returns the therapy-providing segment of the person support surface (e.g., the support segment 104) to a non-therapy position (e.g., a flat position), if the segment was, immediately prior to block 512, in a therapy-providing position, or allows the therapy-providing segment to remain in the non-therapy position (if the segment was already in a non-therapy, e.g., flat, position). In other words, the system 100 delays the lateral rotation therapy for person 1 if person 2 is not detected as being in the desired therapy enabling state.

In block 516, the system 100 controls the lateral rotation apparatus to a therapy state. To do this, the system 100 transitions the therapy-providing segment of the person support surface (e.g., the support segment 104) to a therapy position (e.g., a progressive lateral tilt angle position), if the segment was, immediately prior to block 516, in a non-therapy-providing position, or allows the therapy-providing segment to remain in the therapy position (if the segment was already in a therapy, e.g., progressive lateral tilt, position). In other words, the system 100 initiates the lateral rotation therapy for person 1 if person 2 is detected as being in the desired therapy enabling state. Conversely, the system 100 terminates or suspends the lateral rotation therapy if either person 1 or person 2 is not in the desired state. For example, if person 2 wakes up or is detected as having a restless sleep, the system 100 may suspend the lateral rotation therapy in block 514. Following block 516, the method 500 may conclude or return to block 510. To initiate or suspend lateral rotation therapy, the system 100 activates or deactivates the actuator(s) 136 by an appropriate amount or for an appropriate duration of time, in order to achieve the desired configuration of the person support surface. For example, the system 100 may turn a motor or an air supply on or off, adjust the power level, or adjust other operating parameters of the actuator 136.

Figure 6:
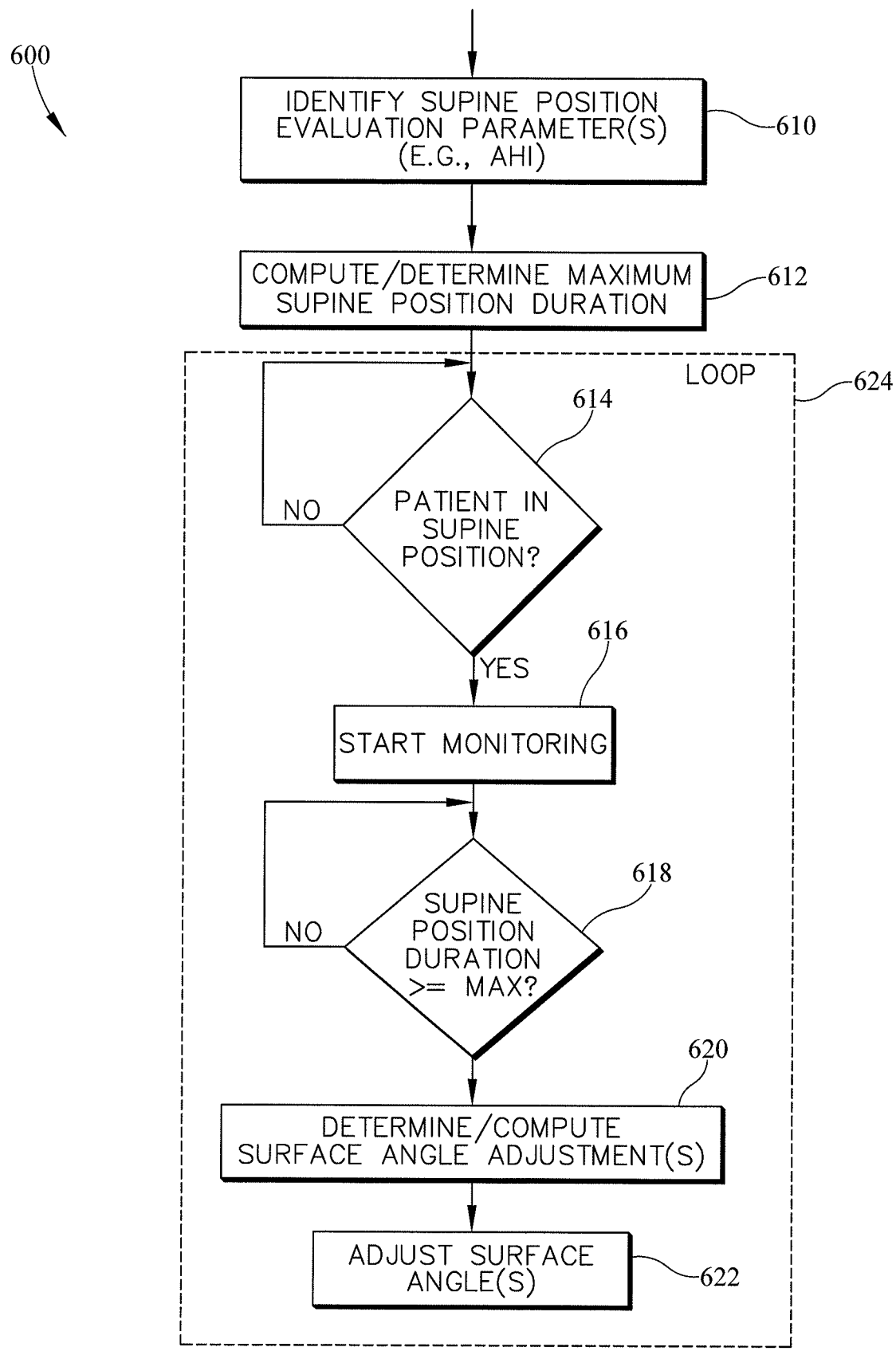
FIG. 6 is a simplified flow diagram of at least one embodiment of a method for controlling a lateral rotation apparatus such as the lateral rotation apparatus shown in FIG. 1 based on supine position duration of an occupant of a dynamic therapy surface such as the dynamic therapy surface of FIG. 1.

Referring now to FIG. 6, an example of a method 600 executable by one or more components of the person support system 100 (e.g., by the supine position control module 166 of the control unit 156), is shown. The method 600 may be embodied as computerized programs, routines, logic and/or instructions, which may be embodied in hardware, software, firmware, or a combination thereof, of the system 100 and/or one or more other systems or devices in communication with the system 100. In block 610, the system 100 identifies one or more supine position evaluation parameters. The supine position evaluation parameters may be defined or selected according to the requirements of a particular design of the system 100, and may include AHI, occupant position, occupant sleep state, and/or other parameters. In block 612, the system 100 computes or determines data indicative of a maximum supine position duration. As used herein, "maximum supine position duration" may refer to, among other things, a maximum amount of time that a person (e.g., a person needing apnea therapy) should spend in the supine position, in order to minimize the risk of occurrence of an apnea event. To determine the maximum supine position duration, the system 100 may query a database or access a lookup table, or read sensed values from, e.g., sensor 140, to obtain a data value indicating the maximum supine position duration based on demographic criteria or patient-specific criteria (such as the patient's AHI score, sleep state, or sleep position). For instance, a sensor 140 may be used to perform real-time (e.g., continuous) monitoring of AHI values (e.g., both supine and non-supine), and the system 100 can adjust the maximum supine position duration and/or tilt angle in response to changes in the AHI score as detected in real-time. In some embodiments, the person's supine AHI and lateral AHI may be used alone or in combination to calculate the maximum supine position duration (and/or other data values used by the control unit 156). In some embodiments, the supine position parameter(s) identified in block 610 may be used to determine or compute the maximum supine position duration in block 612, either statically or dynamically. Following block 612, the illustrative embodiment of system 100 enters a loop 624 in which the system 100 iteratively and dynamically monitors the supine position evaluation parameter(s) and adjusts the lateral rotation apparatus as needed to avoid the occupant's supine position evaluation parameter(s) falling outside an acceptable range (e.g., an AHI score greater than about 5). As such, the system 100 may be configured to dynamically adjust the subject's supine position duration based on his or her current AHI score. Alternatively or in addition, the system 100 may monitor the length of time that the occupant (e.g., person 1 of FIG. 1) spends in the supine position over time, to prevent the length of time in the supine position exceeding the applicable maximum supine position duration. For instance, in the loop 624, the system 100 may implement a fixed maximum supine position duration and simply track the amount of time the occupant spends in the supine position (e.g., by setting a timer) and compare the detected amount of time to the pre-determined maximum supine position duration value (which may be determined based on testing with a representative sample of subjects using the patient support surface in a number of different surface configurations). The system 100 can change the tilt position durations dynamically as well (e.g., as AHI rates change throughout a night of sleep, the amount of time spent in a tilt position can be dynamically adjusted).

In the illustrative embodiment, in block 614, the system 100 determines whether the patient/occupant (e.g., person 1) is in the supine position. To do this, the system 100 may read and analyze data signals from an occupant sensor (e.g., sensor 140) and compare the sensed data values to known values indicative of various patient positions. Alternatively or in addition, the system 100 may determine the current state of the lateral rotation apparatus (e.g., by checking to see whether the bladders 116, 118, 120 are inflated or deflated, or by checking the current operational state of the actuator 136, or by checking to see the current rotational angle of the support sections 116, 118, 120, using, e.g., an angle sensor). If the system 100 does not detect that the patient/occupant is in a supine position, the system 100 remains in block 614. If the system 100 detects that the patient/occupant is in the supine position, the system 100 proceeds to block 616.

In block 616, the system 100 begins monitoring the patient/occupant's supine position evaluation parameter (e.g., AHI, sleep state, or current supine position duration). In block 618, the system 100 determines whether the monitored supine position evaluation parameter indicates that the patient/occupant's supine position duration equals or exceeds the maximum supine position duration. For example, the system 100 may compare the patient/occupant's AHI value to a threshold value or compare the current supine position duration to the maximum supine position duration determined in block 612. Alternatively or in addition, an algorithm may determine the minimum effective tilt angle to reduce AHI to below a threshold value in order to increase compliance by minimizing discomfort caused by a higher tilt angle. The system 100 remains in block 618 if the supine position duration does not exceed the maximum supine position duration value. If the supine position duration equals or exceeds the maximum supine position duration, the system 100 proceeds to block 620.

In block 620, the system 100 determines or computes the surface angle adjustments needed to transition the patient/occupant out of the supine position. To do this, the system 100 may query a database or access a lookup table that maps patient characteristics (such as gender, size, body weight, or AHI) to appropriate surface angles, for example.

In block 622, the system 100 controls the lateral rotation apparatus to make the surface angle adjustments determined or computed in block 620. To do this, the system 100 may activate or deactivate the actuator(s) 136 to rotate one or more of the support sections 116, 118, 120, or inflate or deflate one or more of the bladders 116, 118, 120, by an appropriate amount, to achieve the desired surface angles. It should be noted that the features of the method 600 and more generally, the supine position control module 166, need not be used on a multi-occupant surface. Rather, the features of the method 600 and the supine position control module 166 are applicable to single-person support surfaces, such as those shown in 8-12 and 13A-13D, and can be used in connection with single-person support surfaces in the manner described above. Further, in multi-occupant embodiments, operation of the method 600 and/or the supine position control module 166 may be coordinated with the operation of the multi-occupant control module 164 and method 500. For instance, the method 600 may be initiated as a result of the system 100 determining in block 512 of FIG. 5 that a person 2 is in a therapy-enabling state.

Figure 7:
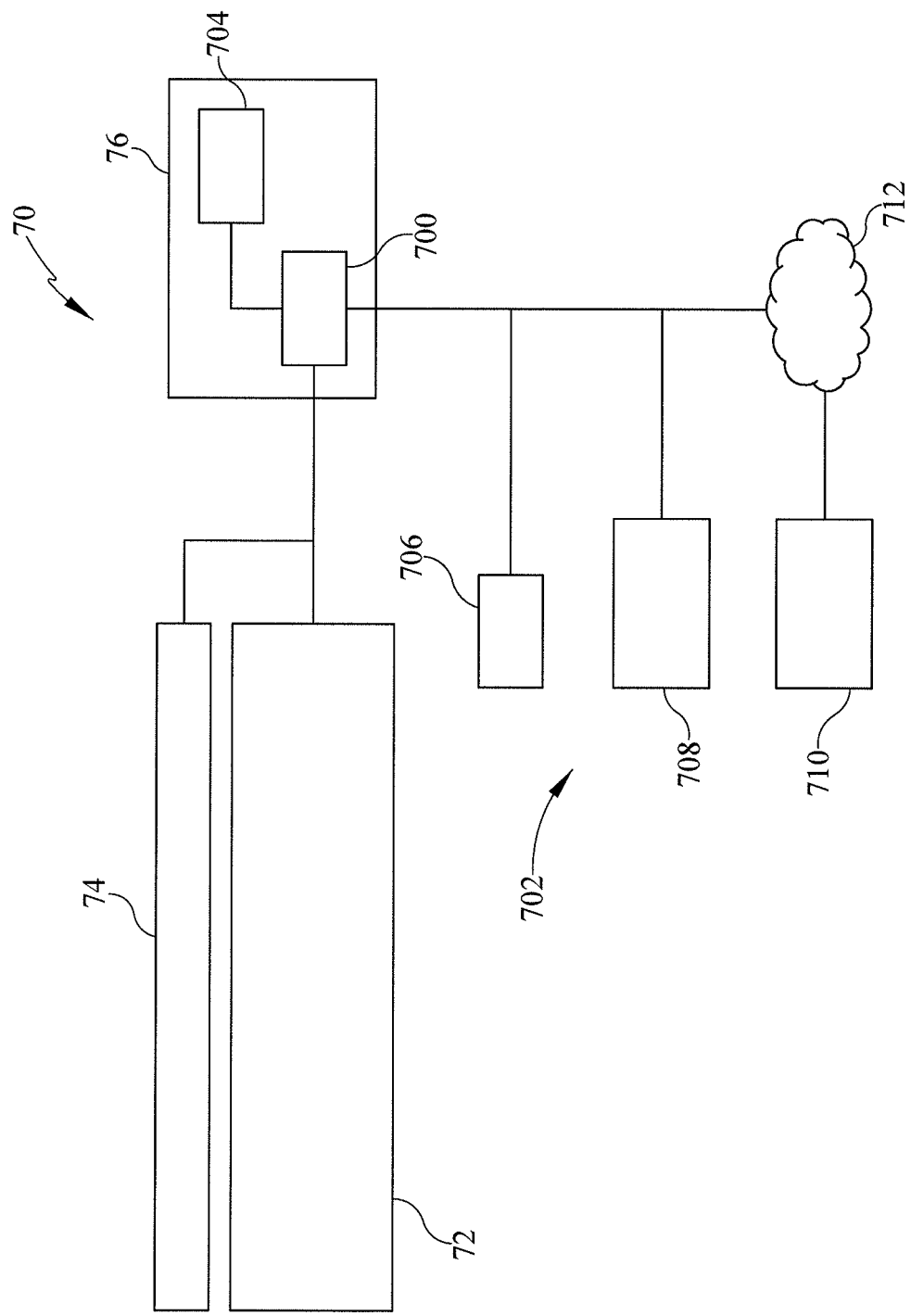
FIG. 7 is a simplified schematic view of at least one embodiment of an adverse event mitigation system, which may include portions of the person support system of FIG. 1 and/or other features disclosed herein.
Figure 8:
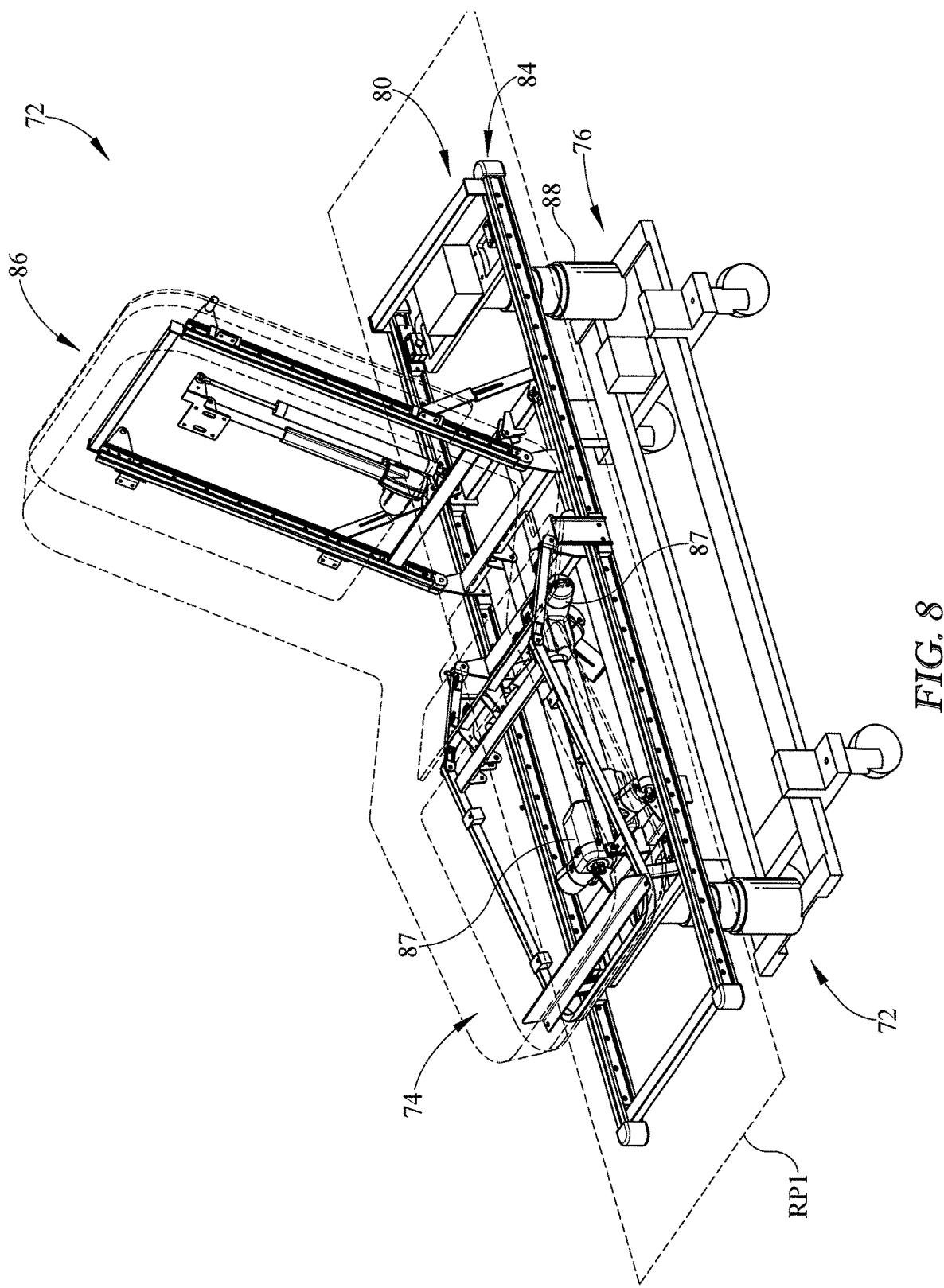
FIG. 8 is a simplified side perspective view of at least one embodiment of a person support apparatus and a person support surface, each or either of which may include one or more of the features disclosed herein.
Figure 10:
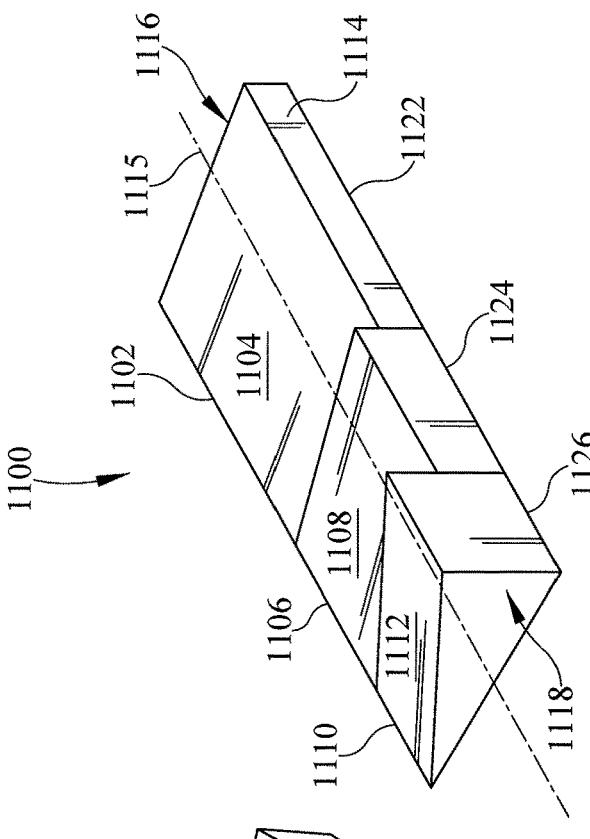
FIG. 10 is another simplified perspective side view of the dynamic therapy surface of FIG. 9, taken from a viewpoint looking toward a longitudinal side opposite the longitudinal side of the viewpoint of FIG. 9.
Figure 11:
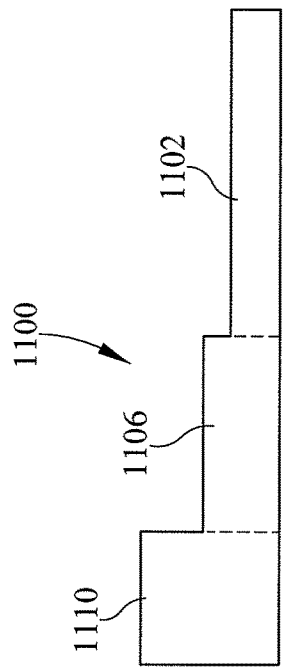
FIG. 11 is a simplified longitudinal elevational view of the dynamic therapy surface of FIG. 9, taken from a viewpoint looking toward the same longitudinal side as the viewpoint of FIG. 10.
Figure 9:
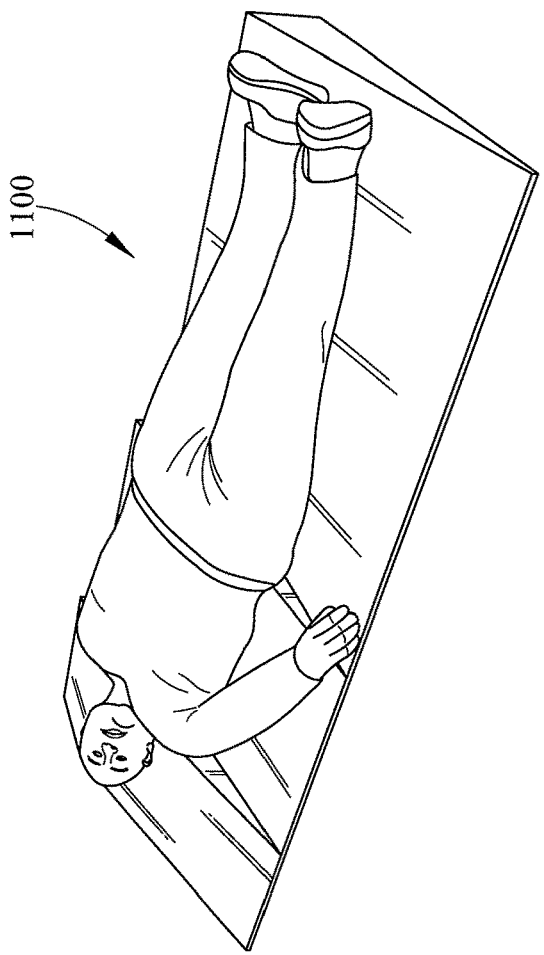
FIG. 9 is a simplified perspective view of at least one embodiment of a dynamic therapy surface that may include one or more of the features disclosed herein, taken from a viewpoint looking toward a longitudinal side of the dynamic therapy surface.
Figure 12:
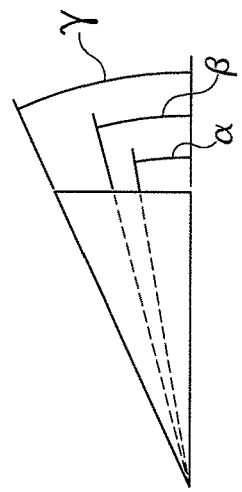
FIG. 12 is a simplified lateral elevational view of the dynamic therapy surface of FIG. 9, taken from a viewpoint near a head end (e.g., element 1118) of the dynamic therapy surface.

Referring now to FIGS. 7-8, an adverse event mitigation system 70 is shown. The illustrative adverse event mitigation system 70 is configured to help reduce the likelihood of an adverse event occurring and/or stop an adverse event in progress. In some contemplated embodiments, the adverse event mitigation system 70 may help reduce the likelihood of obstructive sleep apnea occurring and/or may help stop an obstructive apnea event in progress. In other contemplated embodiments, the adverse event mitigation system 70 may help reduce the likelihood of other adverse events occurring and/or stop other adverse events in progress.

The adverse event mitigation system 70 includes a person support apparatus 72, a person support surface 74 supported on the person support apparatus 72, and a control system 76 as shown in FIG. 7. In some embodiments, the person support apparatus 72 is a hospital bed frame and the person support surface 74 is supported thereon as shown in FIG. 8. In other embodiments, the person support apparatus 72 can be a stretcher, an operating room table, or other person supporting structure (including a consumer-oriented device, such as a lounger or a recliner). The person support apparatus 72 includes a lower frame 87, supports 88 or lift mechanisms 88 coupled to the lower frame 87, and an upper frame 80 movably supported above the lower frame 87 by the supports 88 as shown in FIG. 8. The lift mechanisms 88 are configured to raise and lower the upper frame 80 with respect to the lower frame 87 and move the upper frame 80 between various orientations, such as Trendelenburg and reverse Trendelenburg.

The upper frame 80 includes an upper frame base 84, a deck 86 coupled to the upper frame base 84, and a plurality of actuators 87 coupled to the upper frame base 84 and the deck 86 as shown in FIG. 8. The plurality of actuators 87 are configured to move at least a portion of the deck 86 along at least one of a longitudinal axis, which extends along the length of the upper frame 80, and a lateral axis, which extends across the width of the upper frame 80, between various articulated configurations with respect to the upper frame base 84.

The person support surface 74 is configured to support a person thereon and move with the deck 86 between various configurations including a chair position, a horizontal position, and positions intermediate the horizontal and chair positions. In some embodiments, the person support surface 74 is a hospital bed mattress. In other embodiments, the person support surface 74 is a consumer mattress.

In some embodiments, one or more articulating sections of the deck 86 help move and/or maintain the various portions of the person support surface 74 at different lateral rotation angles (such as the angles α, β and γ shown in the embodiment of FIG. 12) with respect to the reference plane RP1. In the illustrative embodiments, the person support surface 74 is a powered (e.g., dynamic) surface configured to receive fluid (e.g., air) from a fluid supply (e.g., the air supply 136).

The person support surface 74 has a mattress core that can be composed of a single type of material or a combination of materials and/or devices. In the illustrative embodiments, the mattress core includes at least one fluid bladder therein that receives fluid from a fluid supply to maintain the fluid pressure within the fluid bladder at a predetermined level. In some embodiments, the powered surface can include non-powered components, such as a foam frame surrounding or supporting one or more fluid bladders.

In some contemplated embodiments, the mattress core includes dynamically inflatable or static fluid bladders that are configured to support the cervical vertebrae and scapula, respectively, when inflated. The arrangement of the inflatable fluid bladders can vary depending on any number of factors, including, but not limited to, a person's body type and the angle at which the surface is at with respect to the reference plane RP1. In some embodiments, the fluid bladders are configured to laterally tilt the head and/or torso of the occupant. In some embodiments, wedge shaped fluid bladders (not shown) are positioned in head and torso portions of the support surface 74 and are configured to increase the angles of the occupant-contacting surfaces of the head and torso portions, respectively.

In some embodiments, the head and torso of the occupant can be tilted at different angles. For example, the person support apparatus 72 and/or the person support surface 74 can laterally rotate the occupant so that the torso is at an angle in the range of about 10 degrees to about 15 degrees or more, with respect to the reference plane RP1, and the occupant's head is at a non-supine angle (e.g., an angle of about 180° with respect to the reference plane RP1, or, an angle that is not within a range of about 35 to about 45 degrees of vertical orientation). Rotation of the occupant's torso can help the occupant maintain his or her head at a non-supine angle (e.g., an angle of about 180° with respect to the reference plane RP1 or an angle that is not within a range of about 35 to about 45 degrees of vertical orientation).

Portions of the mattress core of the support surface may be composed of a cellular engineered material, such as a single density foam. In some embodiments, the support surface 74 includes multiple zones with different support characteristics configured to, e.g., enhance pressure redistribution as a function of the proportional differences of a person's body. Also, in some embodiments, the mattress core of the support surface 74 includes various layers and/or sections of foam having different impression load deflection (ILD) characteristics, such as may be found in the NP100 Prevention Surface, AccuMax Quantum™ VPC Therapy Surface, and NP200 Wound Surfaces sold by Hill-Rom®.

Referring now to FIG. 7, the control system 76 is configured to change at least one characteristic of the person support apparatus 72 and/or person support surface 74, e.g., to help reduce the likelihood of an adverse event occurring and/or stop an adverse event in progress. The control system 76 includes a processor 700, an input 702, and memory 704. In some embodiments, the input 702 includes a sensor 706, such as, a position sensor, a pressure sensor, a temperature sensor, an acoustic sensor, and/or a moisture sensor, configured to provide an input signal to the processor 700 indicative of a physiological characteristic of the occupant, such as, the occupant's heart rate, respiration rate, respiration amplitude, skin temperature, weight, and position. In some embodiments, the sensors 706 are incorporated into the person support surface 74 or a topper positioned on the person support surface, for example, as disclosed in U.S. Pat. No. 7,515,059 to Price et al. and U.S. Patent Publication No. 2011/0068928 to Riley et al. In some contemplated embodiments, the sensors 706 include, for example, RFID tags, accelerometers, proximity sensors, level sensors, or other physical tracking sensors that may be integrated into or coupled to, for example, ear plugs, ear phones, adhesive sensors, earlobe clips, eye covers, hats, nose strips or other devices that are attached to the patient's head or worn by the patient so that the position/orientation of the patient's head can be tracked. Information captured by monitoring the lateral position of the user's upper respiratory tract has several benefits, including one or more of the following: providing more accurate measurements of the upper respiratory angle for diagnosis of positional obstructive sleep apnea (in one example, sleep labs can use the information to more accurately diagnose POSA); providing biofeedback to help the user to train to maintain a posture that prevents POSA (positional obstructive sleep apnea); tracking performance of the system to determine if the system is achieving a sufficient upper respiratory angle to prevent apnea; monitoring compliance to determine if the system is being used; monitoring the upper respiratory angle and recording the angle when a sleep apnea event occurs; and controlling a surface capable of providing lateral rotation as a function of the inputs from the sensors 706, tracking whether optimal lateral position has been achieved, and controlling the system to achieve a desired head lateral position and/or upper respiratory angle. In some contemplated embodiments, the sensors 706 are tracked by reading devices (i.e., an RFID or radio frequency identification, reader) in a siderail, person support surface, deck, headboard, or location on or in the person support apparatus 70 or person support surface 74, or on or in a headwall in the room or other location in the room. In some contemplated embodiments, the sensor 706 includes a camera positioned at the foot of the bed or above the bed, as disclosed in U.S. Patent Publication No. 2012/0029879 to Sing et al., for example, to track the orientation of the person's head.

In some embodiments, the input 702 includes a user interface 708 configured to receive information from a caregiver or other user. In other embodiments, the input 702 is an Electronic Medical Record (EMR) system 710 in communication with the processor 700 via a hospital network 712. In some embodiments, the processor 700 can output information, automatically or manually upon caregiver input, to the EMR for charting, which can include therapy initiation and termination, adverse event occurrence information, therapy protocol used, caregiver ID, and any other information associated with the occupant, caregiver, person support apparatus 72, person support surface 74, and an adverse event.

The memory 704 stores one or more instruction sets configured to be executed by the processor 700. The instruction sets define procedures that, when executed by the processor, cause the processor 700 to implement one or more protocols that modify the configuration of the person support apparatus 72 and/or the person support surface 14. In one illustrative embodiment, the instruction set defines a proactive procedure that causes the processor 700 to configure the person support apparatus 72 and/or the person support surface 74 in response to an input specifying that the occupant is at risk for sleep apnea. A procedure begins when the processor 700 receives an input signal from the input 702 indicative of the level of risk for an apnea event occurring. In some contemplated embodiments, the level of risk is input from a field in the occupant's EMR. In some contemplated embodiments, the level of risk is input by a caregiver through the user interface, which may arise from a doctor's order or be based on a patient scoring system. In some contemplated embodiments, the level of risk is determined based on a risk score that is calculated by the processor 700 based on a number of factors, including, but not limited to, one or more of the factors listed in TABLE 1 below:

TABLE 1

| Illustrative Risk Factors. | |
| --- | --- |
| Predisposing physical characteristics | BMI in the 95th percentile for age and gender (i.e., 35 kg/m2) 17 inch neck circumference for men (16 inches for women) craniofacial abnormalities that affect the airway anatomical nasal obstructions tonsils that nearly touch or do touch in the medline |
| History of apparent airway obstruction during sleep | loud or frequent snoring observed pauses in breathing while asleep awakening from sleep with a choking sensation frequent arousal from sleep |
| Somnolence | frequent somnolence or fatigue despite getting an adequate amount of sleep falling asleep easily in a nonstimulating place despite adequate sleep |
| Sleep study results | |
| Invasiveness of surgery and anesthesia | superficial under local or peripheral nerve block without sedation superficial with moderate sedation or general anesthesia peripheral with spinal or epidural anesthesia and no more than moderate sedation peripheral with general anesthesia airway surgery with moderate sedation major surgery with general anesthesia airway surgery with general anesthesia |
| Requirement of postoperative opioids | none low-dose oral opioids high-dose oral opioids or neuraxial or parenteral opioids |
| Estimation of perioperative risk | |
| Sex and age of occupant | Estimated sleep disordered breathing is 9% in women and 24% in men with the prevalence for obstructive sleep apnea being 2% in women and 4% in men. The percentages likely increase for older and more obese people |

In some embodiments, the position and/or the orientation of the occupant with respect to patient facing surface of the person support surface 74 is detected and can influence how the person support surface 74 and/or the person support apparatus 72 are configured to move the occupant to the desired position. For example, if the occupant is positioned along the left edge of the patient facing surface of the person support surface 74, the protocol will not rotate them to the left. In some contemplated embodiments, the protocol is terminated because the occupant is in the correct position. In some contemplated embodiments, the protocol helps to maintain the occupant in the position. The position of the occupant on the person support surface 74 can be determined a number of ways, including sensing the force distribution on the upper frame 80 utilizing one or more load cells (not shown) coupled to the upper frame 80, calculating the occupant's center of gravity using the one or more load cells, sensing pressures within the fluid bladders, using a camera (not shown) or 3D sensor (not shown), or using other methods.

Similar procedures can be used for a number of other adverse conditions. In some contemplated embodiments, a procedure can be used to determine if a person is at risk for or has gastroesophageal reflux disease and select a protocol that assists the occupant in maintaining a left lateral decubitus position or semi-reclining position while sleeping. In some contemplated embodiments, the procedure can be used to determine if a person is at risk for or has chronic respiratory insufficiency and select a protocol for the caregiver to approve that assists the occupant in maintaining a left lateral decubitus position while sleeping. In some contemplated embodiments, the procedure can be used to determine if a person is at risk for of has allergies to, for example, feather or down filled pillows, cushions or covers, and can alert the caregiver so that they can remove the item. In other contemplated embodiments, the above-described procedure can be used to determine if the person is at risk for or has one or more other conditions, such as, for example, asthma, pregnancy, sleep paralysis or hallucinations, snoring, stroke bruxism, coughing, hypoxaemia in geriatric inpatients, stroke, or tuberculosis, that might be affected negatively by sleeping in the supine position and select a protocol and/or alert the caregiver so that the person support apparatus 72 and/or the person support surface 74 can be configured to maintain the occupant in a desirable position. In some contemplated embodiments, the procedure can be used to change the sleeping position of occupants to help stimulate blood oxygenation, which can undesirably decrease as the occupant remains stationary. Some patients may have a contraindication to be laterally tilted to one side but not the other, and thus rotation will only tilt to the non-contraindicated side. For example, a recent orthopedic procedure on an arm may induce pain when lying on that side, or a collapsed lung may cause pain on one side. Data indicative of these and other types of patient-specific health conditions may be input by a caregiver (e.g., by a user interface of the control unit 156) or by a communications interface with, e.g., an electronic medical records (EMR) system.

Referring now to FIGS. 9-12, a support system 1100 suitable for supporting a user, such as a person, for example, includes plurality of support pieces, namely a first or leg support piece 1102 forming a first support plane 1104, a second or torso support piece 1106 forming a second support plane 1108, and a third or head support piece 1110 forming a third support plane 1112 that collectively define a segmented, multi-plane, laterally angled sleep surface 1114 having progressively greater angles of rotation along a longitudinal axis 1115 of support system 1100, from a first or bottom edge 1116 of sleep surface 1114 to an opposing second or top edge 1118 of sleep surface 1114, resulting in relatively greater rotation of the upper respiratory tract of the user (as necessary for efficacy in preventing obstructive apnea) and relatively lesser rotation in the lower body of the user (resulting in greater comfort and perceived stability by avoiding rotation of a majority of the user's body mass). In alternative embodiments, sleep surface 1114 is formed using any suitable number of support pieces defining corresponding support planes, for example, one support piece forming a smooth contour over a length of sleep surface 1114 from first edge 1116 to opposing second edge 1118 or a plurality of support pieces, such as two support pieces, three support pieces, or more than three support pieces forming a smooth contour over the length of sleep surface 1114.

Unlike conventional positional therapies for the prevention of obstructive sleep apnea, which attempt to manipulate the user's sleep position and/or orientation using rotation of one plane, in certain embodiments the system described herein uses multiple support planes formed by one or more support pieces to laterally rotate the user. For example, in one embodiment, two support pieces provide two separate support planes, with a first support plane defined by the first support piece configured to support the torso and the legs of the user, and a second support plane defined by the second support piece configured to support the neck and the head of the user.

In an alternative embodiment, three support pieces provide three separate support planes, with a first support plane defined by the first support piece configured to support the legs of the user, a second support plane defined by the second support piece configured to support the torso of the user, and a third support plane defined by the third support piece configured to support the head of the user.

In a further alternative embodiment, more than three support pieces, for example, numerous independent support pieces having a length in a longitudinal direction of sleep surface 1114 of 2-18 inches or, more specifically, 4-12 inches, or, even more specifically, 6 inches, provide a corresponding number of separate support planes. Each support piece can be laterally rotated independently of other support pieces to collectively form sleep surface 1114. In a particular embodiment, the numerous support pieces can be combined to form separate support pieces, for example, creating a first support piece having a length of 18 inches in the longitudinal direction at the foot of the support system 1100, an adjacent second support piece having a length of 12 inches in the longitudinal direction, and a third support piece adjacent the second support piece having a length in the longitudinal direction of 6 inches. In these embodiments, the support pieces forming the support planes can be rotated as necessary or desired to achieve an optimal configuration that is clinically effective (i.e., prevents apnea) and demonstrates acceptable tolerance (i.e., allows the user to sleep comfortably). In an alternative embodiment, a continuously sloped sleep surface is formed by a plurality of support pieces without step increases in lateral rotational angle; this is illustrated as a sleep surface with an infinite number of support pieces.

In the embodiments described herein, the length in the longitudinal direction of each support piece and defined support plane (and the resulting location of transitions between support planes) is designed to achieve clinical efficacy and tolerability. Therefore, a specific length can be defined in a number of configurations, including without limitations: (a) generic plane dimensions (e.g., based on average body geometry, a length of a torso section of the user defined so that when an average user's head is supported by a head support piece, a transition between the torso support piece and the leg support piece occurs below the user's S3 vertebrae); (b) customized plane dimensions (e.g., a torso support plane has a suitable length in the longitudinal direction appropriate to the user's leg length, torso length, and/or a distance from the user's shoulder to his/her inseam); or (c) dynamic plane dimensions (e.g., transitions selected on dynamic surface appropriate to user, selection being either user-selected, care-giver defined, or automatically calculated).

In certain embodiments, each support piece defining the corresponding support planes is independently rotatable about an axis extending parallel with a longitudinal axis of the support system. The independent rotation of each support piece allows the caregiver or the user the ability to focus on progressively increasing an angle of rotation in one or more support pieces having support planes positioned to support the torso of the user, and the neck and/or the head of the user. In certain embodiments, an angle of rotation (or lateral rotational angle) at which the one or more support planes defined by the support pieces configured to support the neck and/or the head of the user is positioned is greater than a rotational angle of the one or more support planes defined by the support pieces configured to support the torso of the user, which is greater than a rotational angle at which the one or more support planes defined by the support pieces configured to support the legs of the user is positioned.

In a particular embodiment, the support plane defined by the support piece configured to support the legs and the torso of the user is positioned at a rotational angle of 10° with respect to a base surface of the support piece, while the support plane defined by the support piece configured to support the head of the user is positioned at a rotational angle of 20° with respect to a base surface of the support piece. In an alternative embodiment, a first support plane defined by the support piece configured to support the legs of the user is positioned at a rotational angle of 10° with respect to a base surface of the first support piece, a second support plane defined by a second support piece configured to support the torso of the user is positioned at a rotational angle of 15° with respect to a base surface of the second support piece, and a third support plane defined by the third support piece configured to support the head of the user is positioned at a rotational angle of 20° with respect to a base surface of the third support piece. In alternative embodiments, the support planes can be positioned at any suitable rotational angle including any suitable lateral rotational angle and/or any suitable longitudinal rotational angle.

Referring further to FIGS. 9-12, in a particular embodiment, first support piece 1102 defines support plane 1104 positioned at a lateral rotational angle α of 20° to 30°, or more specifically, 20° to 25°, or, even more specifically, 25° with respect to a base surface 1122 of first support piece 1102. Second support piece 1106 defines support plane 1108 positioned at a lateral rotational angle β of 10° to 20°, or more specifically, 10° to 15°, or, even more specifically, 15°, with respect to a base surface 1124 of second support piece 1106. Third support piece 1110 defines support plane 1112 positioned at a lateral rotational angle γ of 5° to 15°, or more specifically, 10°, with respect to a base surface 1126 of third support piece 1106. Other lateral rotational angles and step increases in lateral rotational angles between each support piece may also be used to achieve a progressive lateral rotational angle.

In some embodiments, each of support pieces 1102, 1106, 1110 are rotatable about longitudinal axis 1115 to provide sleep surface 1114 having a right side slope or, alternatively, a left side slope to allow the user to sleep on his/her right side or left side, respectively. In one embodiment, one or more cylindrical or tubular sections are positioned within at least a portion of first support piece 1102, second support piece 1106, and third support piece 1110 and coaxially aligned with longitudinal axis 1115 to allow each support piece 1102, 1106, 1110 to rotate about longitudinal axis 1115 independently of the other support pieces 1102, 1106, 1110.

In certain embodiments, support pieces 1102, 1106, 1110 are formed of more than one material, for example, two or more materials, such as two foam materials, having different densities, with the less dense material covering the denser material. In this embodiment, the less dense material is laid on the denser material at the respective base surface and the respective support plane of the support piece to allow sleep surface 1114 to function properly, whether with a right side slope or a left side slope. With the denser material sandwiched between the less dense material, the user will be positioned on the less dense material in either the first or the second orientation.

In this embodiment, support system 1100 allows the user to sleep on either his/her right side or left side, based on the user's sleeping preference. This sleeping preference may not be static. For example, if the user has an injury, an ache, or a desire to change his/her sleeping preference, the orientation of sleep surface 1114 can be changed at any time to accommodate the user's sleeping preference. The orientation can be changed from day to day or during the night. Moreover, from a manufacturing standpoint, a versatile support system 1100 prevents having to manufacture and distribute a sleep surface 1114 having a right side slope and a separate sleep surface 1114 having a left side slope, which would increase production and distribution costs. Finally, a potential purchaser would not have to commit to a sleep side before purchasing the product, which might be a deterrent to purchasing the product.

In some embodiments, each support piece 1102, 1106, 1110 includes one or more inflatable fluid bladders configured to contain a fluid, such as air. In this embodiment, a length of each support piece 1102, 1106, 1110 is adjustable by adding fluid or removing fluid from one or more respective fluid bladders. By adding fluid to one or more of the respective fluid bladders, the length of the respective support piece 1102, 1106, 1110 is increased and the length of the respective support plane 1104, 1108, 1112 is also increased. Conversely, removing fluid from one or more of the respective fluid bladders, the length of the respective support piece 1102, 1106, 1110 is decreased and the length of the respective support plane 1104, 1108, 1112 is also decreased. The amount of fluid within the respective fluid bladders can be monitored and controlled electronically or by the user or caregiver using a suitable device including, without limitation, a suitable pneumatic pump or nozzle. In certain embodiments, a coupler, such as one or more snaps or straps, are utilized to maintain the desired amount of fluid within the respective fluid bladders and provide additional support to the respective support plane(s), for example, when the fluid bladders are not inflated.

As described herein, sleep surface 1114 is customizable to anthropometric dimensions of the individual user to facilitate support system 1100 performance that optimizes or matches the design intent—the body position of the user will prevent or limit undesirable sleep apnea episodes and provide improved comfort.

The fluid bladders are inflatable with air or another suitable fluid (which can be drained as desired from within the cavities of the fluid bladders into a reservoir). A fluid supply can be positioned at or near support system 1100, such as on the floor, beneath the bed, or coupled to the bed. The fluid supply is in independent fluid communication with each pair of fluid bladders by an air system to supply a desired amount of fluid to each fluid bladder based on a signal from a control, for example.

Referring now to FIGS. 13A-13D, there are shown views of a mattress 900 according to another illustrative embodiment of the present disclosure. In this embodiment, the mattress 900 comprises a base 902 which supports a head section 904, a torso section 906, a leg section 908, and a bolster 909. The mattress 900 has a longitudinal length l and a lateral width w. A central longitudinal axis, or centerline, a1 runs through the middle of the mattress 900 longitudinally from end to end and a central lateral axis a2 runs through the mattress laterally from side to side. In this embodiment, the mattress 900 is made of polyurethane foam, although the mattress could be made from many other foam (including memory foam or closed cell foam), cloth, and/or fabric materials, and/or structural elements such as springs and air bladders. For example, a viscoelastic foam with an ILD (indention load deflection) rating of about 50 could be used when the angle Ø1 (described below) is from about 25 to about 30 degrees. Depending on the stiffness (ILD) of the material, the angles disclosed herein can be adjusted somewhat. Smaller angles maybe used when a higher ILD (stiffer) material is utilized, and vice versa. In some embodiments, the material comprises foam having an ILD of from about 25 to about 275.

The mattress 900 in this embodiment is coated with three coats of F-874 Muraculon vinyl based coating, and one coat of F-894 Muraculon vinyl based coating. Other coverings can be utilized, including those which preserve the density or durability of the foam, or increase its infection control or antimicrobial properties. In some embodiments, no coatings or coverings could be utilized.

FIG. 13B is a top view of the illustrative embodiment of FIG. 13A looking in the direction labeled 13B in FIG. 13A. As seen in this view, the head section 904 includes a flat top surface 903 and an angled top surface 905 which slants in the lateral direction at an angle relative to the lateral axis a2. The bolster 909 includes a flat top surface 907 and an angled top surface 911 which slants in the longitudinal direction at an angle relative to the longitudinal axis a1. As seen in FIG. 13B, in this embodiment, the bolster 909 extends along the leg section 908 and a portion of the torso section 906, but not along the head section 904. As shown in FIGS. 13A and 13B, a ramping or tapering down of the bolster 909 occurs about midway along the torso section 906 (below the location where the elbow would typically be supported). Accordingly, when this embodiment is used as intended, the head of the patient will typically not migrate adjacent the bolster 909 and will turn sideways at an angle, with a cheek supported by the angled top surface 903, thereby supporting the head at an angle relative to the lateral axis a2.

FIG. 13C is a longitudinal side view (viewed along the longer side) of the illustrative embodiment of FIG. 13A, looking in the direction labeled 13C in FIG. 13B. FIG. 13D is a lateral side view (viewed along the shorter side, or end) of the illustrative embodiment of FIG. 13A, looking in the direction labeled 13D in FIG. 13C. As best seen in FIGS. 13A and 13D, each of the head section 904, torso section 906, and leg section 908 includes an angled top support surface in this embodiment. In particular, the head section 904 includes the angled top surface 905 which slants in the lateral direction, the torso section 906 includes an angled top surface 915 which slants in the lateral direction, and the leg section includes an angled top surface 917 which slants in the lateral direction. The top surface 905 of the head section 904 is intended to support at least a portion of a person's head, and is generally tilted in the lateral direction at a first angle relative the lateral axis a2. The top surface 915 of the torso section 906 is intended to support at least a portion of a person's torso, and is generally tilted in the lateral direction at a second angle relative to the lateral axis a2. The top surface 917 of the leg section 908 is intended to support at least a portion of a person's leg, and is generally tilted in the lateral direction at a third angle relative to the lateral axis a2. In this embodiment, the top surface 905 of the head section 904 is at an angle Ø1 of about 25 degrees, the top surface 915 of the torso section is at an angle Ø2 of about 17.5 degrees, and the top surface 917 of the leg section is at an angle Ø3 of about 10 degrees. In some embodiments, the angle Ø1 is from about 10 to about 30 degrees, and the angle Ø2 is from about 0 to about 25 degrees (such as from about 1 to about 20 degrees). In some embodiments, angle Ø1 is at least about 10 degrees, and in some embodiments is at least about 15 degrees. In some embodiments angle Ø1 is at least 20 degrees, such as from about 20 to about 25 degrees, and the angle Ø2 is at least about 10 degrees, such as from about 10 to about 25 degrees.

In some embodiments, the angle Ø2 is from about 5 to about 15 degrees less than the angle Ø1. In some embodiments, the angle Ø2 is from about 5 to about 10 degrees less than the angle Ø1, and in some embodiments the angle Ø2 is about 7.5 degrees less than the angle Ø1. In some embodiments, the angle Ø2 is from about 15 to about 17.5 degrees. In some embodiments where the head section angle Ø1 is at about 30 degrees, the angle Ø2 is at about 15 to about 22.5 degrees. In some embodiments, such gradual turning by having angle Ø2 be somewhat less than angle Ø1, and somewhat more horizontal, has been found to increase comfort while still promoting a good sleeping position and urging the head turn significantly away from the vertical up direction (e.g., 35 degrees or more in both directions, clockwise and counterclockwise from vertical up, regardless of sleeping position.)

In some embodiments, the angle Ø3 is from about 0 degrees to about 15 degrees. In some embodiments, the angle Ø3 is from about 0 degrees to about 12.5 degrees, and in some embodiments is about 10 degrees. In some embodiments, the angle Ø3 is from about 0 to about 15 degrees less than the angle Ø2. In some embodiments, the angle Ø3 is from about 5 to about 10 degrees less than the angle Ø2, and in some embodiments the angle Ø3 is about 7.5 degrees less than the angle Ø2.

Because the base 902 is flat in this embodiment, on both its top and bottom, these angles Ø1, Ø2, and Ø3 are likewise relative to the base and to the underside of the mattress in this embodiment. In some embodiments, the top surfaces 905, 915, and 917 can be curved or non-linear or otherwise follow a non-straight or smooth path in the longitudinal and/or lateral directions. In such cases, where these angles are nonlinear in the lateral direction, the angle Ø1 of general lateral sloping of the top surface 905 of the head section can be defined by the angle of a line connecting a point defining the lateral start of the head support surface to a point defining its lateral end (laterally directly across, left to right), or a point at the approximate middle of the support surface (or by averaging the angles of all, or a plurality, of such lines, taken along the section). Likewise, the angle Ø2 of general sloping of the top surface 915 of the torso section can be defined by the line connecting the point defining the lateral start of the torso support surface to the point defining its lateral end, or a point at the approximate middle of the support surface (or by averaging the angles of all or a plurality of such lines taken along the section). Furthermore, the angle Ø3 of general sloping of the top surface 917 of the leg section can be defined by the line connecting the point defining the lateral start of the leg support surface to the point defining its lateral end, or a point at the approximate middle of the support surface (or by averaging the angles of all or a plurality of such lines taken along the section).

In this embodiment of FIGS. 13A-D, the head support surface 905 is sized to support a person's head, the torso support surface 915 is sized to support a person's torso, and the leg support surface 917 is sized to support a person's legs. In some embodiments, the head section 904 is from about 5 inches to about 30 inches in length (such as from about 15 to about 25 inches, or at about 20 inches for example), the torso section 906 is from about 15 inches to about 50 inches in length (such as from about 20 to about 35 inches, or at about 24 inches for example), and the leg section is from about 25 inches to about 50 inches in length (such as from about 30 to about 40 inches, or about 35 inches for example).

Figure 14:
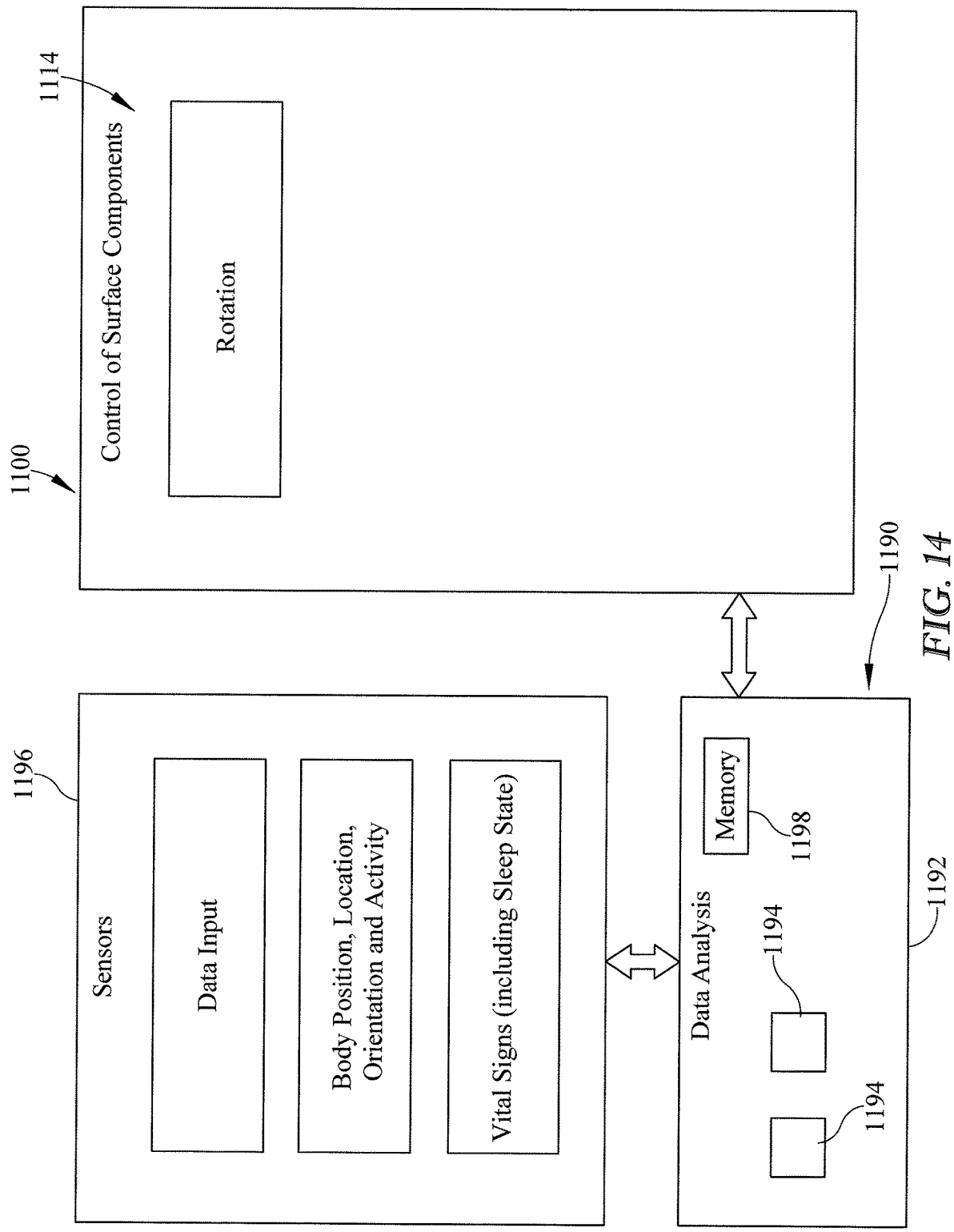
FIG. 14 is a simplified schematic view of components of an exemplary dynamic support system that may include one or more of the features disclosed herein.

Referring now to FIG. 14, support system 1100 includes a suitable computer-implemented control system 1190 operatively coupled to the air system. The computer-implemented control system includes a computer 1192 having one or more processors 1194 and one or more sleep sensors 1196, such as one or more pressure sensors, coupled in signal communication with processors 1194. Sleep sensors 1196 are configured to monitor the user's sleep patterns and transmit signals indicative of the sensed sleep patterns to processors 1194 for manipulation and evaluation of the data. Based at least in part on the one or more signals received from one or more sleep sensors 1196, control system 1190 is configured to inflate or deflate select fluid bladders to reposition the user during sleep to prevent or limit the occurrence of a sleep apnea episode, for example.

Additionally, in certain embodiments, the air system is configured to rest on a conventional mattress or may be configured or reinforced to rest directly on a support structure, such as a bed frame or a floor. With the fluid substantially removed from each of the fluid bladders, the air system can be folded or rolled into a compact configuration to facilitate storing and transporting the air system. In certain embodiments, the air system is less expensive than a conventional mattress and more compact to facilitate portability of support system 1100. Additionally, air system as configured prevents or limits disturbance to the user's partner sleeping next to the user.

The illustrative support system 1100 is a dynamic support system, rather than a static support system, that is configured to control the configuration of sleep surface 1114 based at least in part on data entered into control system 1190 using computer 1192, or another control operatively coupled to computer 1192, and/or sensed by one or more sleep sensors 1196, for example, to improve the performance of sleep surface 1114 in terms of clinical efficacy and user tolerability.

Figure 15:
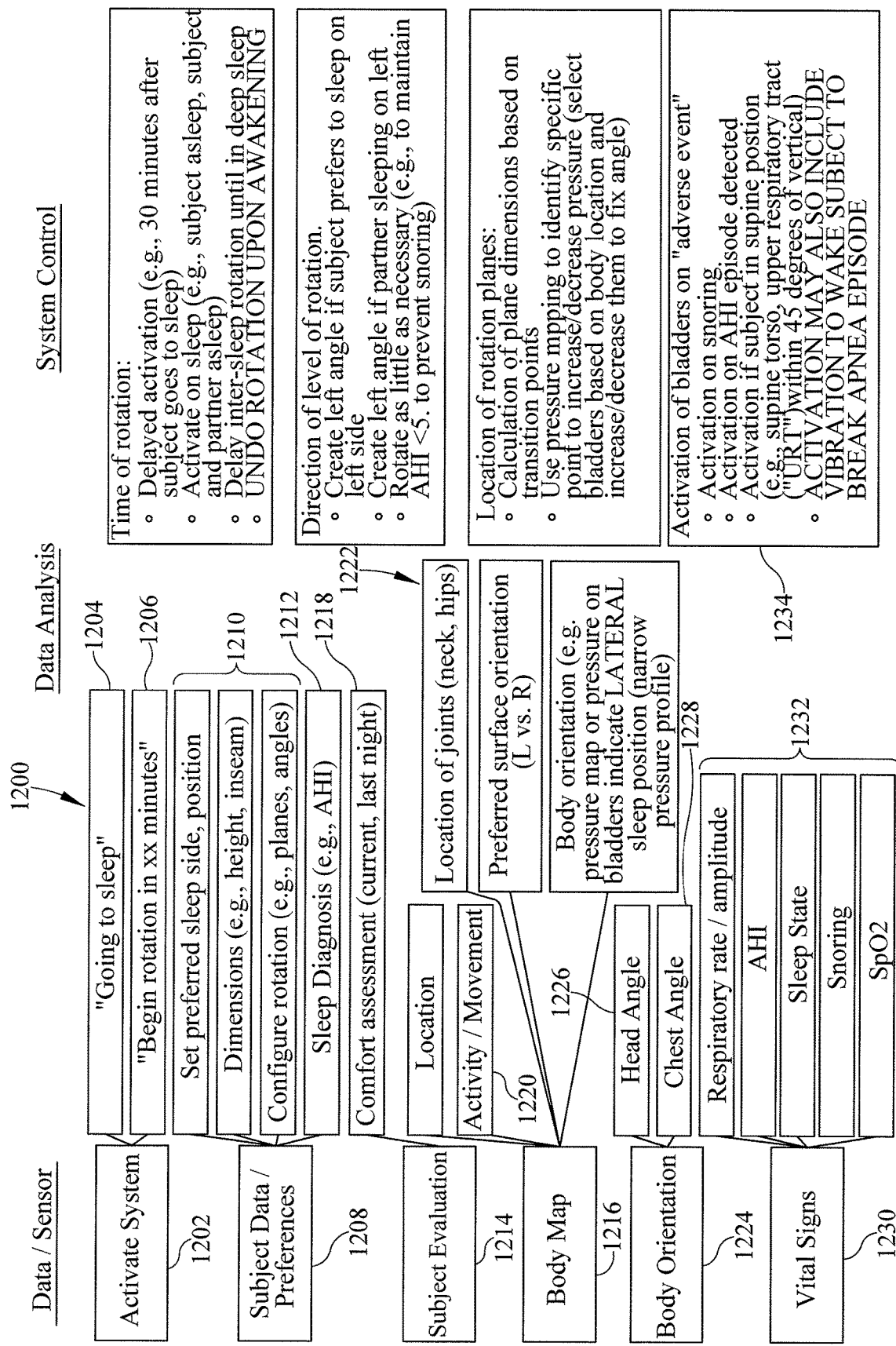
FIG. 15 is a simplified schematic diagram of a method for monitoring sleep activities of a person positioned on a dynamic therapy surface, which may include one or more of the features disclosed herein.

As described herein and shown schematically, for example, in FIGS. 14 and 15, dynamic support system 1100 includes, in addition to other components, a plurality of sleep sensors 1196 configured to sense and monitor various activities including without limitation, the user's body position, a location of the user with respect to sleep surface 1114, an orientation, for example, a left side orientation or a rights side sleep orientation, of the user, the user's vital signs including his/her sleep state, and additional relevant user activity during sleep. Each sleep sensor 1196 is in signal communication with one or more processors 1194 contained within computer 1192 and configured to gather relevant data and generate and transmit to processors 1194 signals indicative of the data gathered. Sleep sensors 1196 are also configured to receive operation control signals from processors 1194.

Within computer 1192, data received from sleep sensors 1196 is analyzed and operational control signals are transmitted to sleep sensors 1196 as well as to other components of support system 1100, such as to fluid supply 1188 to activate fluid supply 1188 to provide air to one or more fluid bladders and/or remove air from one or more fluid bladders to adjust sleep surface 1114 based on signals generated by sleep sensors 1196 and analyzed within computer 1192. In one embodiment, computer 1192 includes suitable memory 1198 to store data sensed and/or generated by control system 1190.

An exemplary method 1200 utilizing control system 1190 for monitoring the sleep activities of a user positioned on support system 1100 is illustrated in FIG. 15. As described above, control system 1190 includes one or more processors 1194 configured to perform the steps as described herein.

Control system 1190 is activated 1202 either manually or automatically to monitor the user's sleep activities and patterns as user begins to sleep. In one embodiment, control system 1190 detects when the user begins to fall asleep 1204 and activates support system 1100 (or a dynamic sleep surface) on a delay 1206 to rotate the user at a suitable time after sleep is detected, such as after the user has been asleep for 30 minutes. In an alternative embodiment, control system 1190 is programmed to activate support system 1100 at a preset time, for example, at a 30 minute delay, without relying on monitoring the user's sleep activity. In a particular embodiment, control system 1190 delays inter-sleep rotation of the user until the user is in a deep sleep. Further, when control system 1190 detects that the user is waking, control system 1190 will activate support system 1100 to move sleep surface 1114 to an initial configuration such that the user can exit from support system 1100. In a further embodiment, control system 1190 prevents activation of support system 1100 if control system 1190 detects the user is sleeping in a lateral decubitus position.

Prior to sleep, the user is able to input 1208 to control system 1190 sleep data 1210 including without limitation, preferred sleeping sides and positions, the user's measurements including, for example, the user's height, weight, and inseam and torso measurements, preferred lateral rotational angles and/or longitudinal rotational angles of one or more support planes defining sleep surface 1114. Based at least in part on the user's input data, control system 1190 is configured to activate support system 1100 to adjust a direction and/or a level of rotation of one or more support planes defining sleep surface 1114. For example, if the user prefers a left side slope to sleep surface 1144, control system 1114 activates fluid bladders within support system 1100 to form the desired lateral left side slope, or if the user's partner is sleeping on the left side of the user, a left angle may be created. In one embodiment, minimal adjustments are made to sleep surface 1114 to maintain the user's AHI under 5 and/or prevent snoring because apneas events and snoring may or may not be equivalent, depending on the user. Additionally, control system 1190 is configured to collected and record data obtained as the user sleeps to diagnose any undesirable or abnormal sleep activities or conditions, including the user's apnea-hypopnea index (AHI), for example.

During sleep, control system 1190 assesses the user's comfort level 1214 and, in a particular embodiment, compares the current evaluation with previous evaluations. The user's body is then mapped 1216 to map body region locations 1218, and user activities and movements 1220 during sleep. The collected data is then analyzed 1222 to determine: the location of joints including, for example, the user's neck, hips, and knees; preferred surface orientation (right side vs. left side orientation); and body orientation (e.g., mapping pressures at various locations on sleep surface 1114 as a result of the user's body orientation, for example, a lateral sleep position indicated by a narrow pressure mapping profile). In one embodiment, location of one or more support planes are calculated and located based on transition points. Under the pressure mapping, specific pressure points are identified to increase or decrease pressure. For example, select fluid bladders are inflated or deflated based on body location and desired lateral rotational angles.

Control system 1190 then assesses 1224 the user's body orientation including, for example a determination of head angle 1226 and chest angle 1228. During sleep, control systems also actively monitors 1230 the user's vital signs, which includes measuring and monitoring the user's respiratory rate and amplitude, AHI, sleep state, snoring, and oxygen saturation ($SpO_2$), for example. If an adverse event is detected, control system 1190 activates 1234 one or more components of support system 1100 to respond appropriately. For example, fluid supply 1188 may be activated to inflate or deflate one or more fluid bladders. Control system 1190 may activate fluid supply 1188 based on one or more of the following events: detection of snoring, detection of an AHI episode (apnea and/or hypopnea), and detection that the user is in a supine position (e.g., supine torso, upper respiratory tract (URT) within 45° of vertical). Control system 1190 may also activate support system 1100 to vibrate to wake the user should control system 1190 detect an adverse event, such as an apnea episode. However, it is not necessary to fully awaken the patient to disrupt apnea episodes; thus, the vibration can be adjusted to the minimal level needed in order to disrupt the apnea event (and thus minimize patient awakenings).

EXAMPLES

Illustrative examples of the technologies disclosed herein are provided below. An embodiment of the technologies may include any one or more, and any combination of, the examples described below.

In an example 1, a dynamic person support system includes a person support surface including a pair of laterally spaced support segments, at least one of the support segments including a lateral rotation apparatus, the lateral rotation apparatus including a plurality of independently rotatable longitudinally arranged support planes and a lateral rotation actuator operably coupled to one or more of the support planes; a first occupant sensor coupled to the support segment including the lateral rotation apparatus; a second occupant sensor coupled to the other support segment; and a control unit including a processor and a non-transitory machine readable storage medium including a dynamic therapy routine, the dynamic therapy routine including instructions executable by the processor to cause the control unit to control the operation of the lateral rotation apparatus by: with the first occupant sensor, detecting a state of a first human subject on the support segment including the lateral rotation apparatus; with the second occupant sensor, detecting a state of a second human subject on the other support segment; and in response to the detected state of the first human subject and the detected state of the second human subject, controlling the lateral rotation actuator of the lateral rotation apparatus.

An example 2 includes the dynamic person support system of example 1, where the lateral rotation actuator includes an electromechanical device configured to drive lateral rotation of the independently rotatable support planes. An example 3 includes the dynamic person support system of example 1 or example 2, where the lateral rotation actuator includes a plurality of inflatable bladders supporting the independently rotatable support planes and an air supply operably coupled to the inflatable bladders. An example 4 includes the dynamic person support system of example 3, where the second occupant sensor is configured to detect a sleep state of the second human subject and the control unit is configured to delay operation of the lateral rotation actuator until the second human subject is detected as being asleep. An example 5 includes the dynamic person support system of any of the preceding examples, where the first occupant sensor is configured to detect a position of the first human subject relative to the support segment including the lateral rotation apparatus, and the control unit is configured to delay operation of the lateral rotation actuator if the detected position of the first human subject is not substantially on the support segment including the lateral rotation apparatus. An example 6 includes the dynamic person support system of any of the preceding examples, where the control unit is configured to control the lateral rotation apparatus based on a combination of criteria including at least one criterion relating to the first human subject and at least one criterion relating to the second human subject. An example 7 includes the dynamic person support system of any of the preceding examples, where the control unit is configured to delay operation of the actuator until both the first human subject and the second human subject are detected as being asleep.

In an example 8, a dynamic person support system, including: a person support surface; a lateral rotation apparatus coupled to the person support surface, the lateral rotation apparatus including a plurality of independently rotatable longitudinally arranged support planes and a lateral rotation actuator operably coupled to one or more of the support planes; a control unit including a processor and a non-transitory machine readable storage medium including a dynamic therapy routine, the dynamic therapy routine including instructions executable by the processor to cause the control unit to control the operation of the lateral rotation apparatus by: determining a maximum supine position duration; monitoring the actual supine position duration of a human subject positioned on the person support apparatus; and controlling the lateral rotation actuator to maintain the actual supine position duration below the maximum supine position duration.

An example 9 includes the dynamic person support system of example 8, where the lateral rotation actuator includes an electromechanical device configured to drive lateral rotation of the independently rotatable support planes. An example 10 includes the dynamic person support system of example 8 or example 9, where the lateral rotation actuator includes a plurality of inflatable bladders supporting the independently rotatable support planes and an air supply operably coupled to the inflatable bladders. An example 11 includes the dynamic person support system of any of examples 8-10, where the control unit is configured to compute the maximum supine position duration as a function of an apnea-hypopnea index (AHI) value of the monitored human subject. An example 12 includes the dynamic person support system of any of examples 8-11, where the control unit is configured to compute the maximum supine position duration and/or tilt angle based on a first apnea-hypopnea index (AHI) value and a second AHI value, where the first AHI value is determined while the human subject is in a supine position and the second AHI value is determined while the human subject is in a non-supine position. An example 13 includes the dynamic person support system of any of examples 8-12, including a sensor in communication with the control unit, where the control unit is configured to receive a sensed value from the sensor and determine the maximum supine position duration based on the sensed value. An example 14 includes the dynamic person support system of example 13, where the sensed value is indicative of an apnea-hypopnea index (AHI) of the monitored human subject. An example 15 includes the dynamic person support system of example 13, where the sensed value is indicative of a sleep state of the monitored human subject. An example 16 includes the dynamic person support system of example 13, where the control unit is configured to adjust the maximum supine position duration in response to the sensed value. An example 17 includes the dynamic person support system of example 14, where the control unit is configured to increase the maximum supine position duration in response to the sensed value being below a threshold value. An example 18 includes the dynamic person support system of example 17, where the control unit is configured to decrease the maximum supine position duration in response to the sensed value being above a second threshold value.

In an example 19, a lateral rotation apparatus includes: a person support surface including head, torso and leg segments each having an independently rotatable person support plane; and a lateral rotation actuator operable to: rotate the head segment to a head tilt angle in the range of about 7 to about 30 degrees relative to a horizontal support plane; and rotate the torso segment to a torso tilt angle that is within a range of about 5 degrees to about 10 degrees less than the head tilt angle.

An example 20 includes the lateral rotation apparatus of example 19, where the lateral rotation actuator includes a plurality of inflatable bladders, and each person support plane is supported by an inflatable bladder. An example 21 includes the lateral rotation apparatus of example 19 or example 20, where the lateral rotation actuator includes an electromechanical device. An example 22 includes the lateral rotation apparatus of any of examples 19-21, where the lateral rotation actuator is operable to rotate the torso segment to a torso tilt angle in the range of about zero to about 25 degrees. An example 23 includes the lateral rotation apparatus of any of examples 19-22, where the lateral rotation actuator is operable to rotate the head segment to a head tilt angle in the range of about 10 to about 15 degrees. An example 24 includes the lateral rotation apparatus of any of examples 19-23, where the lateral rotation actuator is operable to rotate the torso segment to a torso tilt angle in the range of about 5 to about 10 degrees. An example 25 includes the lateral rotation apparatus of any of examples 19-24, where the lateral rotation actuator is operable to rotate the leg segment to a leg tilt angle in the range of about 0 to about 5 degrees. An example 26 includes the lateral rotation apparatus of example 20, including a control unit to control inflation of the bladders to maintain a differential between the head tilt angle and the torso tilt angle, where the differential is in the range of about 5 to about 10 degrees. An example 27 includes the lateral rotation apparatus of any of examples 19-26, where the torso segment is longitudinally longer than the head segment and the leg segment is longitudinally longer than the torso segment. An example 28 includes the lateral rotation apparatus of example 27, where the head segment has a longitudinal length in the range of about 16 inches, the torso segment has a longitudinal length in the range of about 24 inches, and the leg segment has a longitudinal length in the range of about 40 inches. An example 29 includes the lateral rotation apparatus of any of examples 19-28, where the person support surface includes a support material having a density, and the head tilt angle is a function of the density of the support material. An example 30 includes the lateral rotation apparatus of example 29, where the torso tilt angle is a function of the density of the support material.

While certain features have been described in the context of certain illustrative embodiments and examples, it should be understood that such features may be adopted or applied to any of the disclosed embodiments and examples, or to other embodiments and examples.

General Considerations

Portions of the above embodiments may be described in terms of functional block components and various processing steps. Such functional blocks may be realized by any number of hardware and/or software components configured to perform the specified functions. For example, embodiments may employ various integrated circuit components, e.g., memory elements, processing elements, logic elements, look-up tables, and the like, which may carry out a variety of functions under the control of one or more processors, microprocessors or other control devices. Similarly, where the elements of the above embodiments are implemented using software programming or software elements the embodiments may be implemented with any programming or scripting language such as C, C++, Java, assembler, or the like, with the various algorithms being implemented with any combination of data structures, objects, processes, routines or other programming elements. Furthermore, the embodiments can employ any number of conventional techniques for electronics configuration, signal processing and/or control, data processing and the like. Words such as mechanism may be used broadly and are not limited to mechanical or physical embodiments, but can include software routines in conjunction with processors, etc.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical." Numerous modifications and adaptations will be readily apparent to those skilled in this art without departing from the spirit and scope of the embodiments.

The order of execution or performance of the operations in embodiments illustrated and described herein is not essential, unless otherwise specified. That is, the operations may be performed in any order, unless otherwise specified, and embodiments as described may include additional or fewer operations than those disclosed herein. For example, it is contemplated that executing or performing a particular operation before, contemporaneously with, or after another operation is within the scope of aspects of the invention.

Embodiments may be implemented with computer-executable instructions. The computer-executable instructions may be organized into one or more computer-executable components or modules (e.g., hardware, software, firmware, or a combination thereof). Aspects of the disclosure may be implemented with any number and organization of such components or modules. For example, aspects of the disclosure are not limited to the specific computer-executable instructions or the specific components or modules illustrated in the figures and/or described herein. Other embodiments may include different computer-executable instructions or components having more or less functionality than illustrated and described herein.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected.

What is claimed is:

1. A dynamic person support system comprising:
   a person support surface comprising a pair of laterally spaced support segments, at least one of the support segments comprising a lateral rotation apparatus, the lateral rotation apparatus comprising a plurality of independently rotatable longitudinally arranged support planes and a lateral rotation actuator operably coupled to one or more of the support planes;
   a first occupant sensor configured to detect a state of a first human subject supported on the support segment comprising the lateral rotation apparatus;
   a second occupant sensor configured to detect a state of a second human subject supported on the other support segment; and
   a control unit comprising a processor and a non-transitory machine readable storage medium comprising a dynamic therapy routine, the dynamic therapy routine comprising instructions executable by the processor to cause the control unit to control the operation of the lateral rotation apparatus by:
   with the first occupant sensor, detecting the state of the first human subject on the support segment comprising the lateral rotation apparatus;
   with the second occupant sensor, detecting the state of the second human subject on the other support segment; and
   in response to both the detected state of the first human subject and the detected state of the second human subject, controlling the lateral rotation actuator of the lateral rotation apparatus to change a position of the first human subject.

2. The dynamic person support system of claim 1, wherein the lateral rotation actuator comprises an electromechanical device configured to drive lateral rotation of the independently rotatable support planes.

3. The dynamic person support system of claim 1, wherein the lateral rotation actuator comprises a plurality of inflatable bladders supporting the independently rotatable support planes and an air supply operably coupled to the inflatable bladders.

4. The dynamic person support system of claim 3, wherein the second occupant sensor is configured to detect a sleep state of the second human subject and the control unit is configured to delay operation of the lateral rotation actuator until the second human subject is detected as being asleep.

5. The dynamic person support system of claim 1, wherein the first occupant sensor is configured to detect a position of the first human subject relative to the support segment comprising the lateral rotation apparatus, and the control unit is configured to delay operation of the lateral rotation actuator if the detected position of the first human subject is not substantially on the support segment comprising the lateral rotation apparatus.

6. The dynamic person support system of claim 1, wherein the control unit is configured to control the lateral rotation apparatus based on a combination of criteria including at least one criterion relating to the first human subject and at least one criterion relating to the second human subject.

7. The dynamic person support system of claim 1, wherein the control unit is configured to delay operation of the lateral rotation actuator until both the first human subject and the second human subject are detected as being asleep.

8. The dynamic person support system of claim 1, wherein a first sensed value from the first occupant sensor is used by the control unit to determine a maximum supine position duration of the first human subject.

9. The dynamic person support system of claim 8, wherein the first sensed value and a second sensed value from the first and second occupant sensors, respectively, are used by the control unit to determine an apnea-hypopnea index (AHI) of the first and second human subjects, respectively.

10. The dynamic person support system of claim 8, wherein the control unit is configured to adjust the maximum supine position duration of the first human subject in response to the first sensed value.

11. The dynamic person support system of claim 10, wherein the control unit is configured to increase the maximum supine position duration of the first human subject in response to the first sensed value being below a threshold value.

12. The dynamic person support system of claim 11, wherein the control unit is configured to decrease the maximum supine position duration of the first human subject in response to the first sensed value, being above a second threshold value.

13. The dynamic person support system of claim 8, wherein in response to expiration of the maximum supine position duration of the first human subject, the control unit signals the lateral rotation actuator to laterally rotate the first human subject out of the supine position.

14. The dynamic person support system of claim 13, wherein the lateral rotation actuator is operated to laterally rotate each support plane of the plurality of support planes by a different amount in the same direction.

15. The dynamic person support system of claim 14, wherein the plurality of support planes includes a head support plane and a torso support plane, and the lateral rotation actuator is operated to laterally rotate the head support plane by a greater amount than the torso support plane is laterally rotated.

16. The dynamic person support system of claim 15, wherein the head support plane is laterally rotated to a head tilt angle in a range of about 7 to about 30 degrees relative to a horizontal plane and the torso support plane is laterally rotated to a torso tilt angle in a range of about 5 degrees to about 10 degrees less than the head tilt angle.

17. The dynamic person support system of claim 15, wherein the torso support plane is longer than the head support plane in a longitudinal dimension of the person support surface.

18. The dynamic person support system of claim 15, wherein the plurality of support planes further comprises a leg support plane and the lateral rotation actuator is operated to laterally rotate the leg support plane by a lesser amount than the torso support plane is laterally rotated.

19. The dynamic person support system of claim 18, where in the leg support plane is laterally rotated to a leg tilt angle in a range of about 0 degrees to about 5 degrees.

20. The dynamic person support system of claim 18, wherein the leg support plane is longer than the torso support plane in a longitudinal dimension of the person support surface.

* * * * *

UNITED STATES PATENT AND TRADEMARK OFFICE
CERTIFICATE OF CORRECTION

PATENT NO. : 11,007,097 B2
APPLICATION NO. : 16/372721
DATED : May 18, 2021
INVENTOR(S) : David L. Ribble et al.

It is certified that error appears in the above-identified patent and that said Letters Patent is hereby corrected as shown below:

On the Title Page

On Page 3, under (56), References Cited, OTHER PUBLICATIONS, First Column, Line 8, delete "Hournal" and insert in its place --Journal--.

On Page 4, under (56), References Cited, OTHER PUBLICATIONS, First Column, Line 20, delete "Otorhinolaryngol" and insert in its place --Otorhinolaryngology--.

On Page 4, under (56), References Cited, OTHER PUBLICATIONS, Second Column, Line 11, delete "Otorhinolaryngol" and insert in its place --Otorhinolaryngology--.

On Page 5, under (56), References Cited, OTHER PUBLICATIONS, Second Column, Line 49, delete "Otolaryngol" and insert in its place --Otolaryngology--.

Signed and Sealed this
Twentieth Day of July, 2021

Drew Hirshfeld
*Performing the Functions and Duties of the
Under Secretary of Commerce for Intellectual Property and
Director of the United States Patent and Trademark Office*